(12) United States Patent
Hester et al.

(10) Patent No.: US 10,864,035 B2
(45) Date of Patent: Dec. 15, 2020

(54) EUSTACHIAN TUBE MODIFICATION

(71) Applicant: Aerin Medical, Inc., Sunnyvale, CA (US)

(72) Inventors: Jerome Hester, Menlo Park, CA (US); Andrew Frazier, Sunnyvale, CA (US); Gregory Ng, San Leandro, CA (US); Scott J. Wolf, Menlo Park, CA (US)

(73) Assignee: Aerin Medical, Inc., Sunnyvale, CA (US)

( * ) Notice: Subject to any disclaimer, the term of this patent is extended or adjusted under 35 U.S.C. 154(b) by 489 days.

(21) Appl. No.: 15/449,322

(22) Filed: Mar. 3, 2017

(65) Prior Publication Data

US 2017/0252089 A1 Sep. 7, 2017

Related U.S. Application Data

(60) Provisional application No. 62/303,711, filed on Mar. 4, 2016.

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1485* (2013.01); *A61B 18/20* (2013.01); *A61B 17/24* (2013.01); *A61B 18/0218* (2013.01); *A61B 2017/00092* (2013.01); *A61B 2018/00005* (2013.01); *A61B 2018/0022* (2013.01); *A61B 2018/00083* (2013.01);
(Continued)

(58) Field of Classification Search
CPC ................... A61F 11/002; A61B 17/24; A61B 2018/00327
See application file for complete search history.

(56) References Cited

U.S. PATENT DOCUMENTS 4,074,718 A * 2/1978 Morrison, Jr. ..... A61B 18/1402
219/145.21
4,887,605 A 12/1989 Angelsen et al.
(Continued)

FOREIGN PATENT DOCUMENTS

CN 101325919 12/2008
WO 199907299 2/1999
(Continued)

OTHER PUBLICATIONS

Buckley et al., "High-resolution spatial mapping of shear properties in cartilage," J Biomech., Mar. 3, 2010;43(4):796-800, Epub Nov. 5, 2009.
(Continued)

*Primary Examiner* — Linda C Dvorak
*Assistant Examiner* — Ryan T Clark
(74) *Attorney, Agent, or Firm* — Merchant & Gould P.C.

(57) ABSTRACT

Disclosed embodiments relate to devices, systems, and methods of shaping, shrinking, opening, dilating, stiffening, or otherwise modifying a Eustachian tube and its surrounding tissue in order to improve the Eustachian tube's function. For example, patients with blocked, closed, or hypertrophic Eustachian tubes may be able to achieve improved function including easier equalization of pressure between the inner ear and environment.

6 Claims, 31 Drawing Sheets

(51) Int. Cl.
  *A61B 18/20* (2006.01)
  *A61B 17/24* (2006.01)
  *A61B 17/00* (2006.01)
  *A61F 11/00* (2006.01)
  *A61B 18/00* (2006.01)
  *A61B 18/02* (2006.01)
  *A61B 18/04* (2006.01)

(52) U.S. Cl.
  CPC ............ *A61B 2018/00327* (2013.01); *A61B 2018/00565* (2013.01); *A61B 2018/00577* (2013.01); *A61B 2018/00595* (2013.01); *A61B 2018/00642* (2013.01); *A61B 2018/00821* (2013.01); *A61B 2018/00875* (2013.01); *A61B 2018/046* (2013.01); *A61B 2018/126* (2013.01); *A61B 2018/1253* (2013.01); *A61B 2018/143* (2013.01); *A61B 2018/1467* (2013.01); *A61F 11/002* (2013.01)

(56) References Cited

U.S. PATENT DOCUMENTS

| | | | |
|---|---|---|---|
| 5,348,008 | A | 9/1994 | Bomn et al. |
| 5,533,499 | A | 7/1996 | Johnson |
| 5,542,916 | A | 8/1996 | Hirsch et al. |
| 5,624,439 | A | 4/1997 | Edwards et al. |
| 5,674,191 | A | 10/1997 | Edwards et al. |
| 5,707,349 | A | 1/1998 | Edwards |
| 5,718,702 | A | 2/1998 | Edwards |
| 5,728,094 | A | 3/1998 | Edwards |
| 5,730,719 | A | 3/1998 | Edwards |
| 5,733,280 | A | 3/1998 | Avitall |
| 5,738,114 | A | 4/1998 | Edwards |
| 5,743,870 | A | 4/1998 | Edwards |
| 5,743,904 | A | 4/1998 | Edwards |
| 5,746,224 | A | 5/1998 | Edwards |
| 5,800,429 | A | 9/1998 | Edwards |
| 5,807,306 | A | 9/1998 | Shapland et al. |
| 5,816,095 | A | 10/1998 | Nordell, II et al. |
| 5,817,049 | A | 10/1998 | Edwards |
| 5,820,580 | A | 10/1998 | Edwards et al. |
| 5,823,197 | A | 10/1998 | Edwards |
| 5,827,277 | A | 10/1998 | Edwards |
| 5,843,021 | A | 12/1998 | Edwards et al. |
| 5,843,077 | A | 12/1998 | Edwards |
| 5,846,235 | A | 12/1998 | Pasricha et al. |
| 5,879,349 | A | 3/1999 | Edwards |
| 5,938,659 | A | 8/1999 | Tu |
| 6,045,549 | A | 4/2000 | Smethers et al. |
| 6,096,033 | A | 8/2000 | Tu et al. |
| 6,102,907 | A | 8/2000 | Smethers et al. |
| 6,109,268 | A | 8/2000 | Thapliyal et al. |
| 6,126,657 | A | 10/2000 | Edwards et al. |
| 6,131,579 | A | 10/2000 | Thorson et al. |
| 6,139,546 | A | 10/2000 | Koenig et al. |
| 6,152,143 | A | 11/2000 | Edwards |
| 6,165,173 | A | 12/2000 | Kamdar et al. |
| 6,179,803 | B1 | 1/2001 | Edwards et al. |
| 6,210,355 | B1 | 4/2001 | Edwards et al. |
| 6,228,079 | B1 | 5/2001 | Koenig |
| 6,231,569 | B1 | 5/2001 | Bek et al. |
| 6,293,941 | B1 | 9/2001 | Strul et al. |
| 6,309,386 | B1 | 10/2001 | Bek |
| 6,371,926 | B1 | 4/2002 | Thorson et al. |
| 6,383,181 | B1 | 5/2002 | Johnston et al. |
| 6,391,028 | B1 | 5/2002 | Fanton et al. |
| 6,416,491 | B1 | 7/2002 | Edwards et al. |
| 6,425,151 | B2 | 7/2002 | Barnett |
| 6,431,174 | B1 | 8/2002 | Knudson et al. |
| 6,451,013 | B1 | 9/2002 | Bays et al. |
| 6,502,574 | B2 | 1/2003 | Stevens |
| 6,551,310 | B1 | 4/2003 | Ganz et al. |
| 6,562,036 | B1 | 5/2003 | Ellman et al. |
| 6,575,969 | B1 | 6/2003 | Rittman et al. |
| 6,589,235 | B2 | 7/2003 | Wong et al. |
| 6,659,106 | B1 | 12/2003 | Hovda et al. |
| 6,911,027 | B1 | 6/2005 | Edwards et al. |
| 6,978,781 | B1 | 12/2005 | Jordan |
| 7,055,523 | B1 | 6/2006 | Brown |
| 7,097,641 | B1 | 8/2006 | Arless et al. |
| 7,114,495 | B2 | 10/2006 | Lockwood, Jr. |
| 7,322,993 | B2 | 1/2008 | Metzger et al. |
| 7,416,550 | B2 | 8/2008 | Protsenko et al. |
| 7,442,191 | B2 | 10/2008 | Hovda et al. |
| 7,678,069 | B1 | 3/2010 | Baker et al. |
| 7,780,730 | B2 | 8/2010 | Saidi |
| 7,824,394 | B2 | 11/2010 | Manstein |
| 7,850,683 | B2 | 12/2010 | Elkins et al. |
| 8,088,122 | B2 | 1/2012 | Li et al. |
| 8,128,617 | B2 | 3/2012 | Bencini et al. |
| 8,137,345 | B2 | 3/2012 | McNall, III et al. |
| 8,317,781 | B2 | 11/2012 | Owens et al. |
| 8,317,782 | B1 | 11/2012 | Ellman et al. |
| 8,718,786 | B2 | 5/2014 | Shalev |
| 8,936,594 | B2 | 1/2015 | Wolf et al. |
| 8,986,301 | B2 | 3/2015 | Wolf et al. |
| 9,072,597 | B2 | 7/2015 | Wolf et al. |
| 9,125,677 | B2 | 9/2015 | Sobol |
| 9,179,964 | B2 | 11/2015 | Wolf et al. |
| 9,179,967 | B2 | 11/2015 | Wolf et al. |
| 9,237,924 | B2 | 1/2016 | Wolf et al. |
| 9,452,087 | B2 | 1/2016 | Holm et al. |
| 9,415,194 | B2 | 8/2016 | Wolf et al. |
| 9,433,463 | B2 | 9/2016 | Wolf et al. |
| 9,452,010 | B2 | 9/2016 | Wolf et al. |
| 9,486,278 | B2 | 11/2016 | Wolf et al. |
| 9,526,571 | B2 | 12/2016 | Wolf et al. |
| 9,687,288 | B2 | 6/2017 | Saadat |
| 9,687,296 | B2 | 6/2017 | Wolf et al. |
| 9,763,723 | B2 | 9/2017 | Saadat |
| 9,763,743 | B2 | 9/2017 | Lin |
| 9,788,886 | B2 | 10/2017 | Wolf et al. |
| 9,801,752 | B2 | 10/2017 | Wolf et al. |
| 9,888,957 | B2 | 2/2018 | Wolf et al. |
| 9,913,682 | B2 | 3/2018 | Wolf et al. |
| 9,943,361 | B2 | 4/2018 | Wolf et al. |
| 10,028,780 | B2 | 7/2018 | Wolf et al. |
| 10,028,781 | B2 | 7/2018 | Saadat |
| 2002/0016588 | A1 | 2/2002 | Wong et al. |
| 2002/0049464 | A1 | 4/2002 | Donofrio et al. |
| 2002/0087155 | A1 | 7/2002 | Underwood et al. |
| 2002/0128641 | A1 | 9/2002 | Underwood et al. |
| 2003/0144659 | A1 | 7/2003 | Edwards |
| 2003/0208194 | A1 | 11/2003 | Hovda et al. |
| 2003/0208250 | A1 | 11/2003 | Edwards et al. |
| 2003/0225403 | A1 | 12/2003 | Woloszko et al. |
| 2004/0220644 | A1 | 11/2004 | Shalev et al. |
| 2005/0020901 | A1 | 1/2005 | Belson |
| 2005/0119643 | A1 | 6/2005 | Sobol et al. |
| 2005/0222565 | A1 | 10/2005 | Manstein |
| 2005/0234439 | A1 | 10/2005 | Underwood |
| 2005/0240147 | A1 | 10/2005 | Makower et al. |
| 2005/0288665 | A1 | 12/2005 | Woloszko et al. |
| 2006/0235377 | A1 | 10/2006 | Earley |
| 2006/0253117 | A1 | 11/2006 | Hovda et al. |
| 2006/0276817 | A1 | 12/2006 | Vassallo et al. |
| 2007/0066944 | A1 | 3/2007 | Nyte |
| 2007/0073282 | A1 | 3/2007 | McGarrigan et al. |
| 2007/0219600 | A1 | 9/2007 | Gertner et al. |
| 2008/0027423 | A1 | 1/2008 | Choi et al. |
| 2008/0027480 | A1 | 1/2008 | van der Burg et al. |
| 2008/0082090 | A1 | 4/2008 | Manstein |
| 2008/0125626 | A1 | 5/2008 | Chang et al. |
| 2008/0154343 | A1 | 6/2008 | Li et al. |
| 2008/0312644 | A1 | 12/2008 | Fourkas et al. |
| 2009/0018485 | A1 | 1/2009 | Krespi et al. |
| 2009/0124958 | A1 | 5/2009 | Li |
| 2009/0143821 | A1 | 6/2009 | Stupak |
| 2009/0163890 | A1* | 6/2009 | Clifford .............. A61B 1/227 604/514 |
| 2009/0292358 | A1 | 11/2009 | Saidi |
| 2010/0144996 | A1 | 6/2010 | Kennedy et al. |
| 2010/0152730 | A1 | 6/2010 | Makower et al. |

(56) References Cited

U.S. PATENT DOCUMENTS

| | | |
|---|---|---|
| 2010/0174283 A1 | 7/2010 | McNall |
| 2010/0241112 A1 | 9/2010 | Watson |
| 2010/0262133 A1 | 10/2010 | Hoey et al. |
| 2011/0009737 A1 | 1/2011 | Manstein |
| 2011/0282268 A1 | 11/2011 | Baker et al. |
| 2012/0039954 A1 | 2/2012 | Cupit et al. |
| 2012/0078377 A1 | 3/2012 | Gonzales et al. |
| 2012/0298105 A1 | 11/2012 | Osorio |
| 2012/0316473 A1 | 12/2012 | Bonutti et al. |
| 2012/0316557 A1 | 12/2012 | Sartor et al. |
| 2012/0323227 A1* | 12/2012 | Wolf ............... A61B 18/1485 606/2 |
| 2012/0323232 A1 | 12/2012 | Wolf et al. |
| 2013/0218158 A1 | 8/2013 | Danek et al. |
| 2014/0088463 A1 | 3/2014 | Wolf et al. |
| 2014/0114233 A1 | 4/2014 | Deem et al. |
| 2015/0202003 A1 | 7/2015 | Wolf et al. |
| 2016/0287315 A1 | 10/2016 | Wolf et al. |
| 2016/0354136 A1 | 12/2016 | Saadat |
| 2016/0361112 A1 | 12/2016 | Wolf et al. |
| 2017/0007316 A1 | 1/2017 | Wolf et al. |
| 2017/0014258 A1 | 1/2017 | Wolf et al. |
| 2017/0095288 A1 | 4/2017 | Wolf et al. |
| 2017/0209199 A1 | 7/2017 | Wolf et al. |
| 2017/0231651 A1 | 8/2017 | Dinger et al. |
| 2017/0245924 A1 | 8/2017 | Wolf et al. |
| 2017/0252100 A1 | 9/2017 | Wolf et al. |
| 2017/0360495 A1 | 12/2017 | Wolf et al. |
| 2018/0000535 A1 | 1/2018 | Wolf et al. |
| 2018/0177542 A1 | 6/2018 | Wolf et al. |
| 2018/0177546 A1 | 6/2018 | Dinger et al. |
| 2018/0185085 A1 | 7/2018 | Wolf et al. |
| 2018/0228533 A1 | 8/2018 | Wolf et al. |
| 2018/0263678 A1 | 9/2018 | Saadat |
| 2018/0317997 A1 | 11/2018 | Dinger et al. |

FOREIGN PATENT DOCUMENTS

| | | |
|---|---|---|
| WO | 2001043653 | 6/2001 |
| WO | WO 2003024349 | 3/2003 |
| WO | 2007037895 | 4/2007 |
| WO | 2007134005 | 11/2007 |
| WO | 2010077980 | 7/2010 |
| WO | 2012174161 | 12/2012 |
| WO | 2015047863 | 4/2015 |
| WO | 2015048806 | 4/2015 |
| WO | 2015153696 | 10/2015 |

OTHER PUBLICATIONS

Buckley et al., "Mapping the depth dependence of shear properties in articular cartilage," J Biomech., 41(11):2430-2437, Epub Jul. 10, 2008.

Cole, "Biophysics of nasal airflow: a review," Am J Rhinol., 14(4):245-249, Jul.-Aug. 2000.

Cole, "The four components of the nasal valve," Am J Rhinol., 17(2):107-110, Mar.-Apr. 2003.

Griffin et al., "Effects of enzymatic treatments on the depth-dependent viscoelastic shear properties of articular cartilage," J Orthop Res., 32(12):1652-1657, Epub Sep. 5, 2014.

International Search Report and Written Opinion for PCT/US15/023742, dated Jun. 29, 2015, 5 pages.

International Search Report and Written Opinion for PCT/US2012/042316, dated Aug. 24, 2012, 15 pages.

International Search Report and Written Opinion for PCT/US2014/054726, dated Dec. 23, 2014, 5 pages.

Kjaergaard et al., "Relation of nasal air flow to nasal cavity dimensions," Arch Otolaryngol Head Neck Surg., 135(6):565-570, Jun. 2009.

Silverberg et al., "Structure-function relations and rigidity percolation in the shear properties of articular cartilage," Biophys J., 107(7):1721-1730, Oct. 7, 2014.

Singapore Search Report for Application Serial No. 201309238-2, dated Jun. 9, 2014 for pp. 1-27.

Stewart et al., "Development and validation of the Nasal Obstruction Symptom Evaluation (NOSE) scale," Otolaryngol Head Neck Surg., 130(2):157-163, Feb. 2004.

Stupak, "Endonasal repositioning of the upper lateral cartilage and the internal nasal valve," Ann Otol Rhinol Laryngol., 120(2):88-94, Feb. 2011.

Stupak, MD, H.D., A Perspective on the Nasal Valve, Dept. of Otorhinolaryngology, Albert Einstein College of Medicine, Nov. 6, 2009.

International Search Report and Written Opinion for PCT/US2017/020677, dated Jun. 16, 2017, 14 pages.

International Search Report and Written Opinion for PCT/US2017/017415, dated May 2, 2017, 12 pages.

* cited by examiner

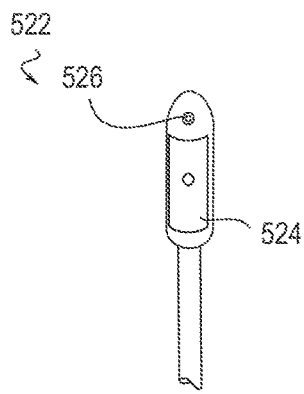
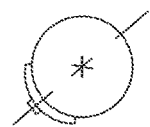
FIG. 9A    FIG. 9B
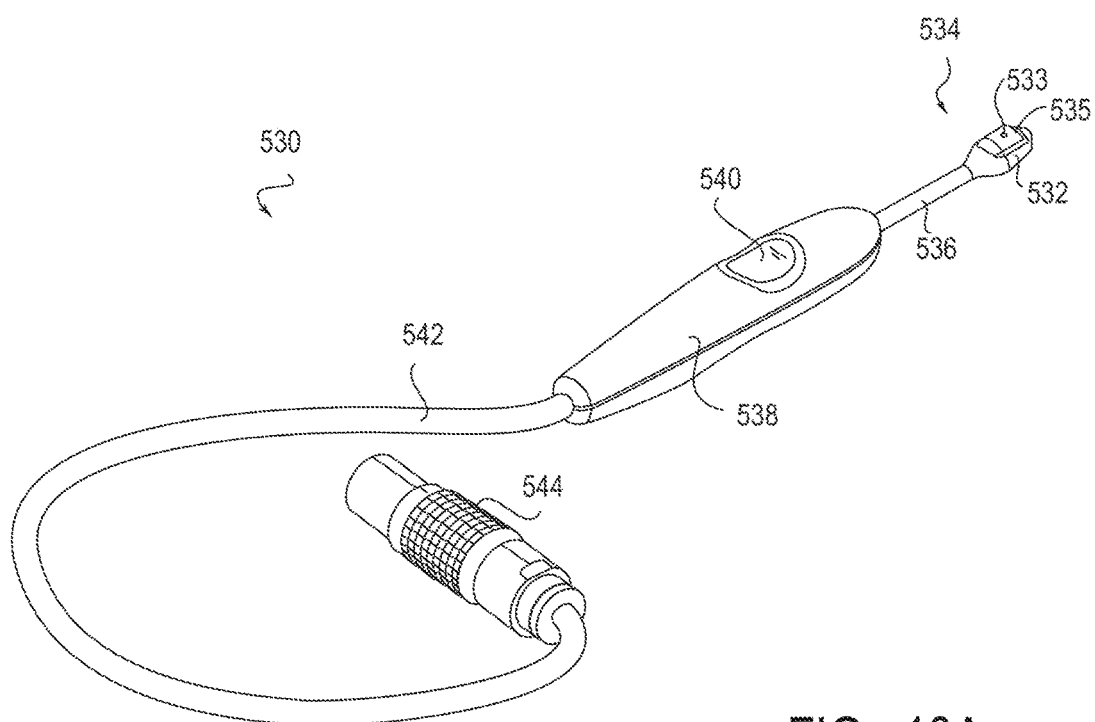
FIG. 10A

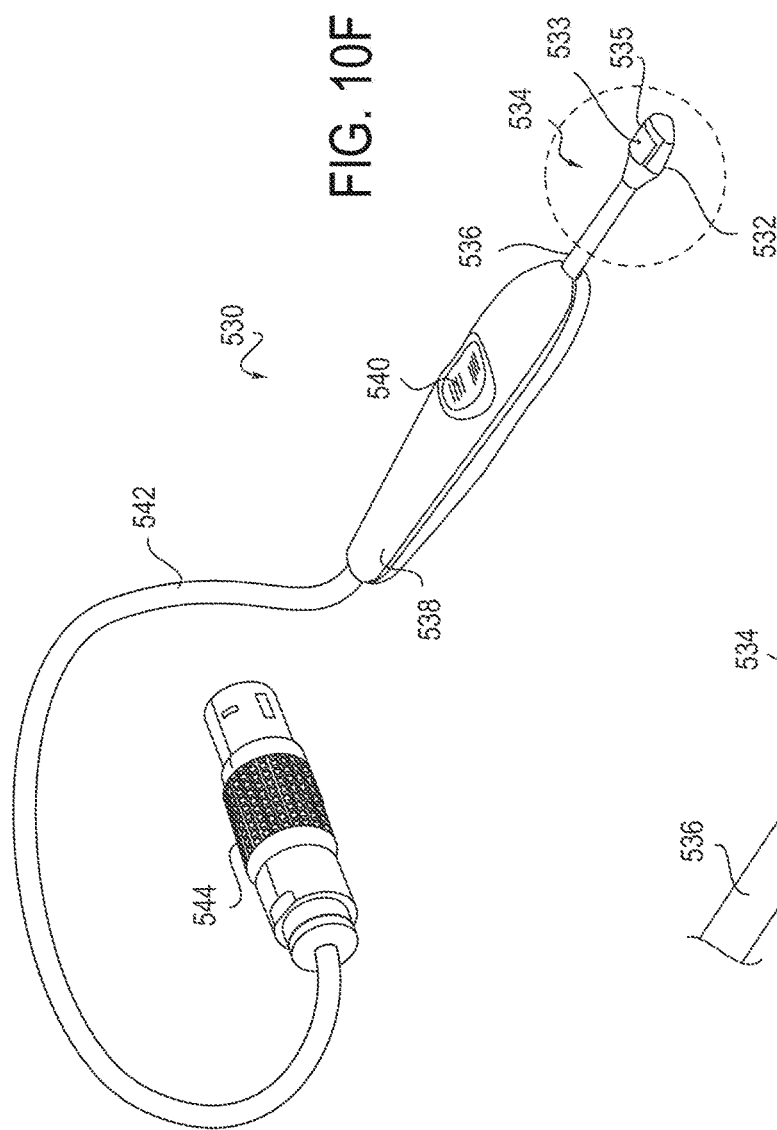

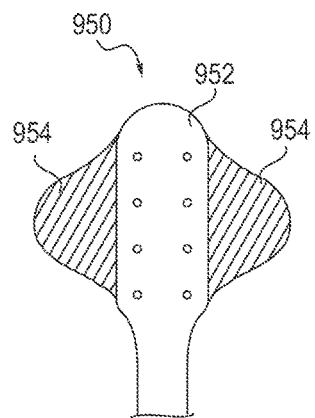
FIG. 22
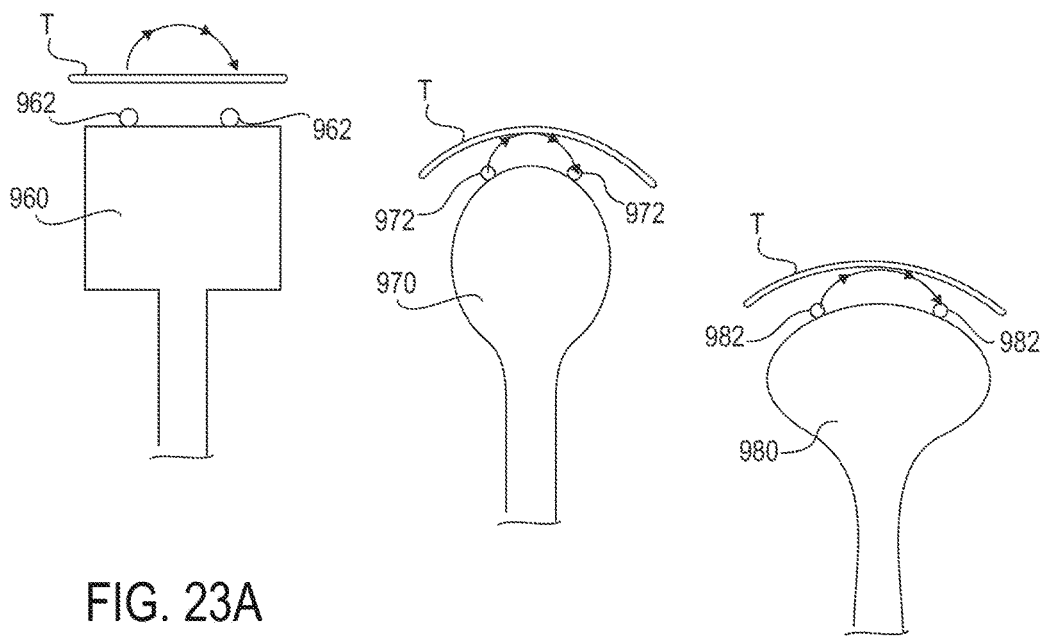
FIG. 23A
FIG. 23B
FIG. 23C

EUSTACHIAN TUBE MODIFICATION

CROSS-REFERENCE TO RELATED APPLICATIONS

This application claims the benefit of U.S. Provisional Application Ser. No. 62/303,711, titled "Eustachian Tube Modification," filed on Mar. 4, 2016. The disclosure of this priority application is hereby incorporated by reference in its entirety herein.

FIELD

This application generally relates to the field of medical devices and treatments, and in particular to systems, devices and methods for treating a Eustachian tube and/or surrounding tissue.

BACKGROUND

As shown in FIG. 1, the Eustachian tube (sometimes referred to as the auditory tube or the pharyngotympanic tube) is a tube that connects the tympanic cavity of the middle ear to the nasopharynx. At the nasopharynx, the Eustachian tube is bounded by the torus of the Eustachian tube and forms the pharyngeal opening of the Eustachian tube (also known as the pharyngeal ostium). The Eustachian tube includes a cartilaginous portion and an osseous (bone) portion. There are several muscles that affect the function of the Eustachian tube, including muscles of the soft palate (e.g., the levator veli palatini and tensor veli palatini) and muscles of the ear (e.g., tensor tympani).

Dysfunction of the Eustachian tube (e.g., caused by inflammation of the tissue of or near the Eustachian tube) may result in Eustachian tube blockage and/or cause the Eustachian tube to resist opening. This may result in undesirable pressure changes and fluid collection in the middle ear. This can result in discomfort and may cause ear infections. While sometimes dysfunction of the Eustachian tube may resolve on its own or with minimal intervention, sometimes greater intervention is required. Some methods require modifying the ear drum or installing a prosthesis in the Eustachian tube or surrounding tissue. Current methods have drawbacks relating to patient discomfort and ineffectiveness. For example, implantable tubes often hold the Eustachian tube in an always-open state, which may be very distracting and uncomfortable for patients. Further, implantable tubes or surgical intervention can require general anesthesia, invasive surgical access, and other comorbidities.

Therefore, a need exists for improved methods, systems, and devices for modifying a patient's Eustachian tube to help treat Eustachian tube malfunction. Ideally, such methods, systems, and devices would be minimally invasive or less invasive than currently available methods. Also ideally, such methods, systems, and devices would not result in a permanently open Eustachian tube. The embodiments described herein are relevant to achieving at least some of these objectives.

BRIEF SUMMARY

Embodiments of the present application are relevant to devices, systems, and methods for the treatment of Eustachian tubes. An example method may include contacting an elongate treatment element of a treatment device against or in proximity to the Eustachian tube. Example methods may further include applying energy using the elongate treatment element, thereby modifying the Eustachian tube. Example methods may further include the Eustachian tube retaining the modification after the elongate treatment element is removed.

In one aspect, a method of treating a Eustachian tube may involve: contacting an elongate treatment element of a treatment device with tissue in or near the Eustachian tube; and applying energy to or removing energy from at least one of the tissue or an underlying tissue beneath the tissue, using the elongate treatment element, to modify at least one property of the Eustachian tube, thereby treating the Eustachian tube. The at least one property of the Eustachian tube may remain at least partially modified after the treatment.

In various embodiments, the applying energy using the elongate treatment element may include applying bipolar radiofrequency energy. In some embodiments, applying energy using the elongate treatment element includes applying bipolar radiofrequency energy to mucosa near an ostium in a nasopharynx. In some embodiments, the at least one property includes an amount of contraction the muscles of the Eustachian tube require to open the Eustachian tube. In some embodiments, the method may further involve applying sufficient force to the tissue with the treatment element to temporarily reshape the tissue at least one of before, during or after applying the energy. In some embodiments, the elongate treatment element has a convex tissue treatment surface; and force is applied to the tissue with the convex tissue treatment surface to cause the tissue to assume a concave shape. In some embodiments, contacting the elongate treatment element includes contacting atraumatic, rounded electrodes on a tissue treatment surface of the treatment element with the tissue.

In another aspect, a method of modifying a Eustachian tube may involve: contacting an elongate treatment element of a treatment device against mucosa of the patient's nasopharynx; and applying energy to or removing energy from the mucosa or tissue underlying the mucosa, thereby causing a modification of the Eustachian tube. The Eustachian tube may at least partially maintain the modification after the treatment element is removed and the mucosa or tissue underlying the mucosa heals.

In some embodiments, applying energy to or removing energy from the mucosa or tissue underlying the mucosa further involves: applying energy to the tissue underlying the mucosa; and removing energy from the mucosa. In some embodiments, removing energy from the mucosa further includes cooling the mucosa using a cooling mechanism of the treatment element. In some embodiments, applying energy to the tissue underlying the mucosa involves injuring the tissue underlying the mucosa. In some embodiments, contacting the treatment element of the treatment device against mucosa of the patient's nasopharynx involves contacting the treatment device against the mucosa with sufficient force to alter a shape of the mucosa. In some embodiments, applying energy includes applying radiofrequency energy. In some embodiments, the mucosa is near a pharyngeal opening of the Eustachian tube. In some embodiments, the tissue underlying the mucosa includes one or more of cartilage of the Eustachian tube, bone of the Eustachian tube, the torus of the Eustachian tube, muscles that affect the function of the Eustachian tube, muscles of the soft palate, levator veli palatini muscle, tensor veli palatini muscle, muscles of the ear, and the tensor tympani muscle. In some embodiments, modifying the Eustachian tube includes shaping, shrinking, opening, dilating, or stiffening the Eustachian tube.

In another aspect, a method of modifying a Eustachian tube, includes positioning a treatment element within a patient's nasopharynx adjacent to target tissue to be treated; and delivering radiofrequency energy to the electrode to heat the target tissue, thereby modifying a property of the target tissue and a property of the Eustachian tube. In some embodiments, the treatment element has a convex treatment surface and an electrode. In some embodiments, the property of the target tissue and the property of the Eustachian tube remain at least partially modified after the treatment element is removed.

In some embodiments, delivering radiofrequency energy includes delivering radiofrequency energy to at least one of: cartilage of the Eustachian tube, bone of the Eustachian tube, the patient's upper airway, the patient's nose, the patient's pharyngeal opening of the Eustachian tube, the patient's torus of the Eustachian tube, muscles that affect the function of the Eustachian tube, muscles of the patient's soft palate, a levator veli palatini muscle, a tensor veli palatini muscle, muscles of the patient's ears, and a tensor tympani muscle. In some embodiments, the method further includes cooling the target tissue or tissue near the target tissue before, during, or after delivering the radiofrequency energy. In some embodiments, delivering radiofrequency energy includes delivering radiofrequency energy for about 15 seconds to about 1 minute. In some embodiments, delivering radiofrequency includes heating an area of tissue around the electrode to a temperature of about 50 degrees C. to about 70 degrees C. In some embodiments, positioning the treatment element includes applying force to a tissue of the patient's nasopharynx.

In another aspect, a method of treating a Eustachian tube having a pharyngeal ostium, the method includes: positioning an array of energy delivery elements of a treatment element around the pharyngeal ostium; and applying energy using the energy delivery elements to modify the tissue of the ostium, surrounding mucosa, or surrounding submucosa. In some embodiments, positioning an array of energy delivery elements around the pharyngeal ostium includes inserting a flexible probe into the pharyngeal ostium, thereby aligning the array of energy-delivery elements around the pharyngeal ostium.

In another aspect, a device for modifying a Eustachian tube has: a shaft; a treatment portion extending from a distal end of the shaft, the treatment portion having an arcuate tissue treatment surface; a first arcuate row of electrodes disposed on the arcuate tissue treatment surface; a second arcuate row of electrodes disposed on the tissue treatment surface; and a thermocouple disposed between the first arcuate row and the second arcuate row.

In some embodiments, the device may further include a passive positioner extending from the treatment portion. In some embodiments, the passive positioner component is sized and shaped to be inserted into an opening of the Eustachian tube to facilitate positioning the one or more electrodes relative to the opening. In some embodiments, the passive positioner includes a flexible elongate protrusion having a bulb at a distal end of the protrusion. In some embodiments, one or more electrodes are disposed on the passive positioner for treatment within the Eustachian tube. In some embodiments, the one or more electrodes disposed on the treatment surface include multiple electrodes disposed on the treatment surface circumferentially around the passive positioner. In some embodiments, the shaft is an elongate, flexible shaft sized and shaped to be inserted through a patient's nostril to reach the opening of the Eustachian tube. In some embodiments, the passive positioner has an expandable balloon configured to be expanded after the passive positioner is inserted into the Eustachian tube to facilitate positioning or anchoring the device relative to the opening of the Eustachian tube. In some embodiments, the electrodes of the first row and the electrodes of the second arcuate row comprise elongate, blunt-tipped electrodes extending away from the tissue treatment surface.

These and other aspects and embodiments will be described in further detail below, in reference to the attached drawing figures.

BRIEF DESCRIPTION OF THE DRAWINGS

FIGS. 9A and 9B illustrate an embodiment of a device for applying energy to tissue, the device having a symmetrical shape.

FIGS. 10A-10G illustrate an embodiment of a device for applying energy to tissue using a monopolar electrode.

FIG. 22 is a bottom view of a distal end of a treatment device, illustrating wings of the treatment device that may be used to help guide the distal end to a desired location.

FIGS. 23A-23C are top views of various alternative embodiments of distal ends of treatment devices having different shapes for addressing differently shaped tissues.

DETAILED DESCRIPTION

Disclosed systems, methods, and devices may be used to modify a Eustachian tube of a patient. In some embodiments, a device may be used to shape, shrink, open, dilate, stiffen, or otherwise modify the Eustachian tube or surrounding tissue in order to improve the Eustachian tube's function. In some embodiments, modifying the Eustachian tube includes causing a change in the Eustachian tube or surrounding tissue that makes the Eustachian tube easier to open. In some embodiments, modifying the Eustachian tube includes changing the shape of the Eustachian tube.

In some embodiments, some treatment methods may include applying treatments selected to change mechanical or structural properties of the treated tissue. In some embodiments, such treatments may include application of energy to, or removal of energy from, target tissue. Some embodiments may include injecting bulking agents, glues, polymers, collagen and/or other allogenic or autogenic tissues, or growth agents.

Embodiments may include a treatment element that is held against or in proximity to the Eustachian tube and/or surrounding tissue and used to modify the tissue. In one embodiment, a device or system applies bipolar radiofrequency energy to the mucosa near an ostium of the Eustachian tube in the nasal cavity to heat, shrink, and/or stiffen the tissue, thus allowing the muscles of the Eustachian tube to require less contraction in order to open the tube. In another embodiment, the device may have a cryogenic treatment element. The device may treat a portion of the ostium or the entire ostium at once with an array of electrodes. In some embodiments, an energy-modifying balloon may treat the ostium or Eustachian tube. In some embodiments, electrodes delivering monopolar or bipolar energy are atraumatic, rounded electrodes that press against the target tissue. In some embodiments, electrodes are needles that penetrate the mucosa.

While the Eustachian tube may be directly modified in some embodiments, alternative devices, systems, and methods may indirectly target the Eustachian tube by modifying tissues that are associated with the Eustachian tube (e.g., surrounding tissues). For example, the tensor veli palatini muscle connects to the lateral wall of cartilage of the Eustachian tube. Some embodiments may treat the tensor veli palatini muscle to cause a change in the function of the Eustachian tube, without directly modifying the Eustachian tube. In some embodiments, disclosed methods may be applied without requiring general anesthesia. The treatment element may be configured to be inserted through the nostril to the treatment area. In some embodiments, treatment is applied without incisions, dissections and/or other significant trauma.

Example Method of Modifying the Eustachian Tube

Figure 2:
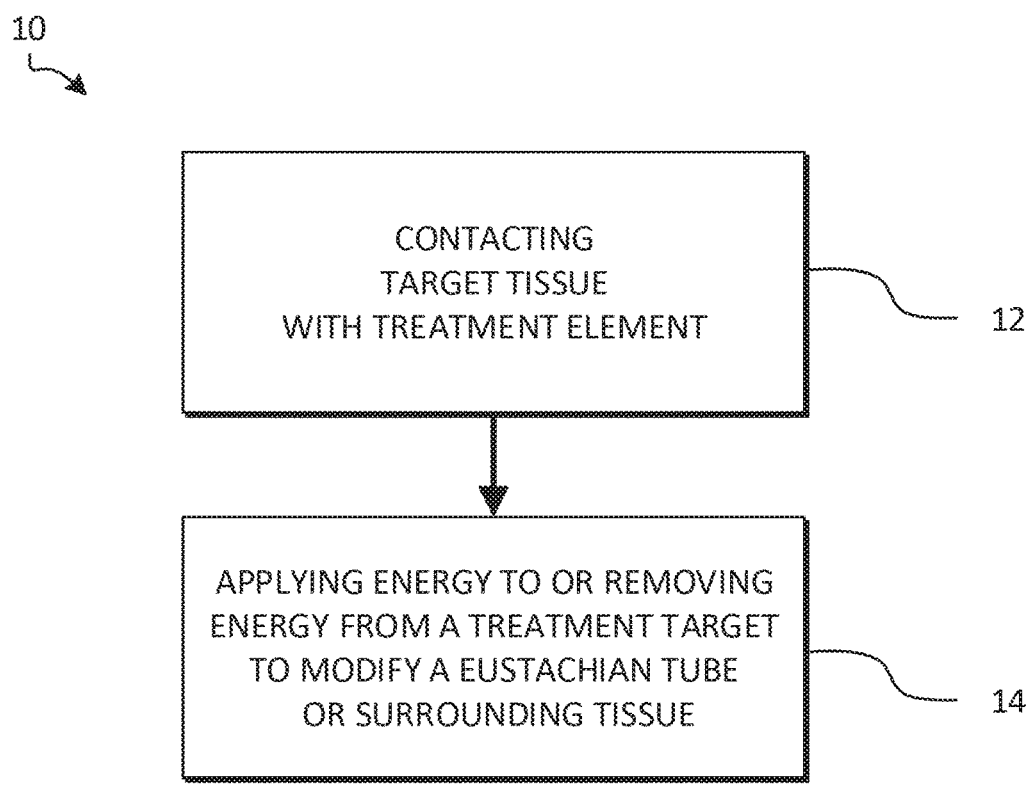
FIG. 2 illustrates an example method of modifying a Eustachian tube.

FIG. 2 illustrates an example method 10 to modify a Eustachian tube and surrounding tissue. The example method 10 may include one or more steps or actions as illustrated by one or more of blocks 12 and/or 14. The operations or actions described in the blocks 12, 14 may be performed by a healthcare provider or other person and may include using systems and devices disclosed herein or elsewhere.

An example method may begin with block 12, which recites "contacting target tissue with treatment element." Block 12 may be followed by block 14, which recites "applying energy to or removing energy from a treatment target to modify a Eustachian tube or surrounding tissue." The blocks included in the described example methods are for illustration purposes. In alternative embodiments, the various blocks may be divided into additional blocks, supplemented with other blocks, or combined together into fewer blocks. Other variations of these specific blocks are contemplated, including changes in the order of the blocks, changes in the content of the blocks being split or combined into other blocks, and so on.

Block 12 recites "contacting target tissue with treatment element." The target tissue may be any tissue at or through which energy can be applied to or removed from in order to modify a Eustachian tube or surrounding tissue (see block 14). In some embodiments, the target tissue may be any tissue (e.g., skin, mucosa, submucosa, cartilage, bone, or other tissue) at, near, or associated with: the ear, the ear canal, the middle ear, the tympanic cavity of the middle, the Eustachian tube, cartilage of the Eustachian tube, bone of the Eustachian tube, the upper airway, the nose, the nasopharynx, the pharyngeal opening of the Eustachian tube, the torus of the Eustachian tube, muscles that may affect the function of the Eustachian tube, muscles of the soft palate, levator veli palatini muscle, tensor veli palatini muscle, muscles of the ear, the tensor tympani muscle, and others.

In some embodiments, block 12 further includes accessing the target tissue. For example, in some embodiments, the target tissue may located at or near the nasopharynx and block 12 may further include inserting a treatment element of a device through a patient's nostril and placing the treatment element at the target tissue within the nasopharynx. As another example, in some embodiments, the target tissue may be located within the middle ear or the Eustachian tube itself and block 12 may further include inserting a treatment element of a device through a patient's ear canal to a target treatment site. This may further include inserting a treatment element of a device through the patient's ear drum to a target site within the middle ear and/or Eustachian tube.

As a further example, in some embodiments, block 12 may further include creating an incision or other opening in particular tissue and inserting the treatment element through the incision or opening to access a deeper layer of tissue. This may include, for example, creating a perforation in an ear drum and inserting a treatment element to access an inner ear. As another example, this may include creating an incision in mucosa or other tissue and contacting the treatment element against the deeper layer of tissue, such as muscle and/or connective tissue that helps the Eustachian tube open or contract. In some embodiments, the device itself includes a cutting element for creating its own incisions.

Block 14 recites "applying energy to or removing energy from a treatment target to modify a Eustachian tube or surrounding tissue." In some embodiments, energy may be applied in the form of heat, radiofrequency (RF), laser, light, ultrasound (e.g., high intensity focused ultrasound), microwave energy, electromechanical, mechanical force, cooling, alternating or direct electrical current (AC or DC current), chemical, electrochemical, or others. Alternative embodiments may include removing energy from a treatment target by, for example, applying cryogenic therapy. Some embodiments may include both applying energy to and removing energy from tissue.

Any one or more of the above energy-application mechanisms may also be used to reshape, remodel, or change mechanical or physiologic properties of structures of a Eustachian tube or surrounding tissues. For example, in some embodiments, energy may be applied to a targeted region of tissue adjacent a Eustachian tube, such that the tissue modification results in a tightening, shrinking or enlarging of such targeted tissues, resulting in a modification of the Eustachian tube. In some such embodiments, reshaping of a Eustachian tube section may be achieved by applying energy without necessarily applying a mechanical reshaping force. For example energy can be used to selectively shrink tissue in specific locations of the Eustachian tube or surrounding tissues that will lead to a controlled conformational change.

In alternative embodiments, strengthening and/or conformation change (e.g., reshaping) of a Eustachian tube or surrounding tissues may include modification of tissue growth and/or the healing and fibrogenic process. For example, in some embodiments energy may be applied to a targeted tissue at or near the Eustachian tube in such a way that the healing process causes a change to the shape of the Eustachian tube and/or a change in the structural properties of the tissue. In some embodiments, such targeted energy application and subsequent healing may be further controlled through the use of temporary implants or reshaping devices (e.g. internal stents or molds, or external adhesive strips).

In some embodiments, energy may be delivered into the tissue to cause a conformational change and/or a change in the physical properties of the tissue. Energy delivery may be accomplished by transferring the energy through tissue, including but not limited to epithelium, mucosa, sub-mucosa, muscle, ligaments, tendon and/or skin. In some embodiments, energy may also be delivered to tissue using needles, probes or microneedles that pass through tissue (e.g., epithelium, mucosa, submucosa, muscle, ligaments, tendon and/or skin). The treatment element may be used to deform tissue into a desired shape by pressing a convex surface of the treatment element against the tissue to be treated.

A control input such as a button may be used to activate the electrode and deliver energy (e.g., RF energy) to the tissue to be treated. In some embodiments, temperature of the area around an electrode during treatment is from about 30 degrees Celsius to about 90 degrees Celsius. In some embodiments, temperature of the area around the electrode during treatment is from about 40 degrees Celsius to about 80 degrees Celsius. In some embodiments, temperature of the area around the electrode during treatment is from about 50 degrees Celsius to about 70 degrees Celsius. In some embodiments, temperature of the area around the electrode during treatment is about 60 degrees Celsius. In some embodiments, for example during cryotherapy, temperature of the area around the electrode may be lower.

In some embodiments, treating the target tissue includes treatment for about 10 seconds to about 3 minutes. In some embodiments, treating the target tissue includes treatment for about 10 seconds to about 2 minutes. In some embodiments, treating the target tissue includes treatment for about 15 seconds to about 1 minute. In some embodiments, treating the target tissue includes treatment for about 20 seconds to about 45 seconds. In some embodiments, treating the target tissue includes treatment for about 30 seconds.

In some embodiments, treating the target tissue includes delivering between about 1 and about 100 watts to the tissue. In some embodiments, treating the target tissue includes delivering between about 5 watts and about 75 watts to the tissue. In some embodiments, treating the target tissue includes delivering between about 10 watts and about 50 watts to the tissue.

In an embodiment, the method 10 may further include identifying a patient who may benefit from modification of the Eustachian tube and/or surrounding tissue.

In an embodiment, the method may further include positioning the patient either in an upright position (e.g., seated or standing) or lying down. Local anesthesia may be applied to an area near or surrounding the tissue to be treated. General anesthesia may also be used.

In an embodiment, the method may further include using a positioning element to measure a desired depth or angle of treatment. The positioning element may be inserted to the desired depth of treatment and rotated to a desired angle of treatment. Marks along the positioning element can indicate the desired depth. Marks along the base of the shaft of the positioning element can indicate the desired angle. The physician can then insert the treatment device to the desired location. The physician may also assess any other characteristics relevant to the treatment of the patient's ear, nasopharynx, Eustachian tube and/or surrounding tissue that may influence the manner of treatment. In some embodiments, a reshaping element may be used to manipulate tissue into a configuration allowing improved Eustachian tube function; and treatment may be performed while such a reshaping element is maintaining the desired configuration of the Eustachian tube and/or surrounding tissue.

Example Treatment Device

Figure 3:
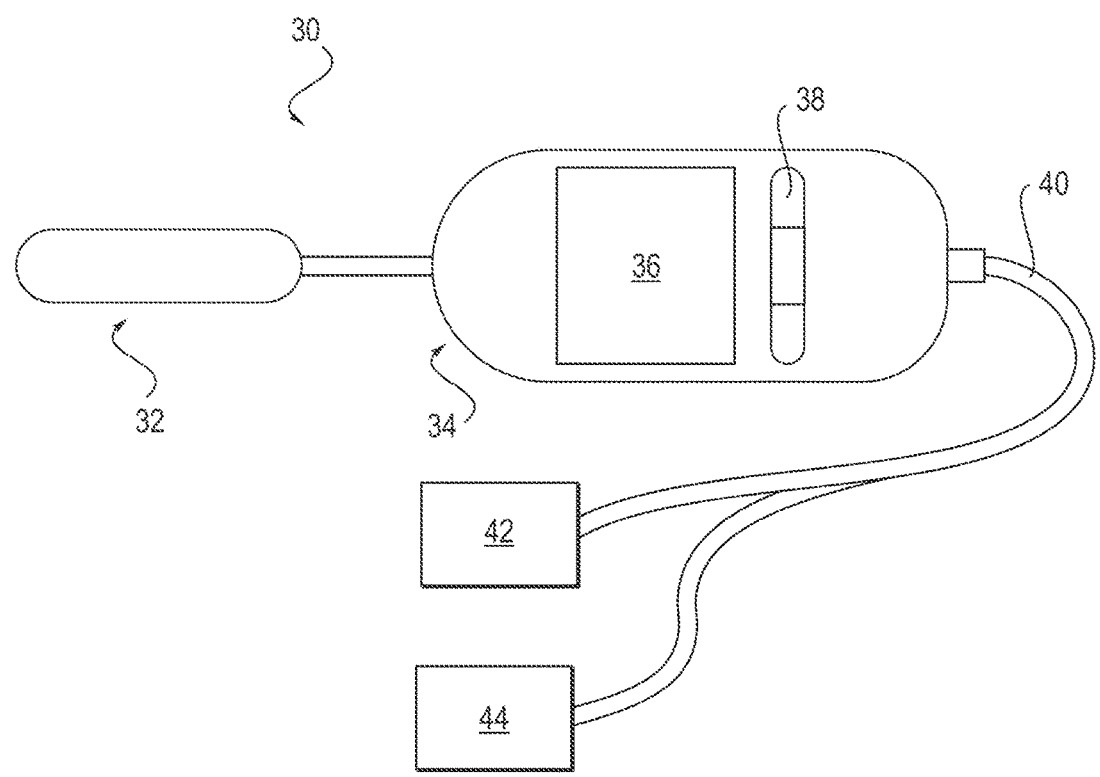
FIG. 3 depicts a schematic illustration of a treatment device according to some embodiments.

FIG. 3 illustrates an embodiment of a treatment device 30. The device 30 includes a treatment element 32 which may be configured to be placed at or near a target tissue to be treated. For example, the device 30 or a portion thereof may be configured to be placed inside a patient's pharynx, nasopharynx, nasal cavity, nasal passage, nasal airway, airway, and/or ear canal to deliver desired treatment. In some embodiments, the device 30 may further include a handle section 34 which may be sized and configured for easy handheld operation by a clinician. In some embodiments, a display 36 may be provided for displaying information to a clinician during treatment.

In some embodiments, the information provided on the display 36 may include treatment delivery information (e.g. quantitative information describing the energy being delivered to the treatment element) and/or feedback information from sensors within the device and/or within the treatment element. In some embodiments, the display may provide information on physician selected parameters of treatment, including time, power level, temperature, electric impedance, electric current, depth of treatment and/or other selectable parameters.

In some embodiments, the handle section 34 may also include input controls 38 (e.g., buttons, knobs, dials, touchpad, joystick, etc.). In some embodiments, controls may be incorporated into the display, such as by the use of a touch screen. In further embodiments, controls may be located on an auxiliary device which may be configured to communicate with the treatment device 30 via analog or digital signals sent over a cable 40 or wirelessly, such as via Bluetooth, Wi-Fi, infrared or any other wired or wireless communication method.

In some embodiments the treatment system may include an electronic control system 42 configured to control the timing, location, intensity and/or other properties and characteristics of energy or other treatment applied to targeted regions of a Eustachian tube or surrounding tissues. In some embodiments, a control system 42 may be integrally incorporated into the handle section 34. Alternatively, the control system 42 may be located in an external device which may be configured to communicate with electronics within the handle section 34. A control system may include a closed-loop control system having any number of sensors, such as thermocouples, electric resistance or impedance sensors, ultrasound transducers, or any other sensors configured to detect treatment variables or other control parameters.

The treatment system may also include a power supply 44. In some embodiments, a power supply may be integrally incorporated within the handle section 34. In alternative embodiments, a power supply 44 may be external to the handle section 34. An external power supply 44 may be configured to deliver power to the handle section 34 and/or the treatment element 32 by a cable or other suitable connection. In some embodiments, a power supply 44 may include a battery or other electrical energy storage or energy generation device. In other embodiments, a power supply may be configured to draw electrical power from a standard wall outlet. In some embodiments, a power supply 44 may also include a system configured for driving a specific energy delivery technology in the treatment element 32. For example, the power supply 44 may be configured to deliver a radio frequency alternating current signal to an RF energy delivery element. Alternatively, the power supply may be configured to deliver a signal suitable for delivering ultrasound or microwave energy via suitable transducers. In further alternative embodiments, the power supply 44 may be configured to deliver a high-temperature or low-temperature fluid (e.g., air, water, steam, saline, or other gas or liquid) to the treatment element 32 by way of a fluid conduit.

In some embodiments, the treatment element 32 may have a substantially rigid or minimally elastic shape sized and shaped such that it substantially conforms to an ideal shape and size for treating target tissue to cause a modification of the Eustachian tube or surrounding tissues. In some embodiments, the treatment element 32 may have a curved shape, either concave or convex with respect to a wall of as patient's nasopharynx. In some embodiments, the shape of a fixed-shape treatment element may be substantially in a shape to be imparted to the target tissue. In some embodiments, the treatment element may be sized and/or shaped to be inserted through a patient's nostril, ear canal, ear drum, and/or other area in order to access a treatment area.

In some embodiments, as shown for example in FIG. 3, the treatment element 32 may include a substantially cylindrical central portion with a semi-spherical or semi-ellipsoid or another shaped end-cap section at proximal and/or distal ends of the treatment element 32. In alternative embodiments, the treatment element may include a substantially ellipsoid shape. In some embodiments, an ellipsoid balloon may have an asymmetrical shape. In alternative embodiments, the treatment element 32 may have an asymmetrical "egg-shape" with a large-diameter proximal end and a smaller-diameter distal end. In some embodiments, the element 32 can be shaped so as to impart a shape to the tissue to be treated. Any suitable solid or expandable medical balloon material and construction available to the skilled artisan may be used.

In some embodiments, the treatment element 32 may be configured to deliver heat energy to the Eustachian tube or surrounding tissues. In such embodiments, the treatment element may include any suitable heating element. For example, the treatment element 32 may include electrical resistance heating elements. In alternative embodiments, the heating element may include conduits for delivering high-temperature fluids (e.g. hot water or steam) onto the Eustachian tube or surrounding tissues. In some embodiments, a high-temperature fluid heating element may include flow channels which place high-temperature fluids into conductive contact with Eustachian tube or surrounding tissues without such fluids directly contacting tissue of the patient. In further embodiments, any other suitable heating element may be provided. In further embodiments, the treatment element 32 may include elements for delivering energy in other forms such as light, laser, RF, microwave, cryogenic cooling, DC current and/or ultrasound in addition to or in place of heating elements.

U.S. Pat. No. 6,551,310 describes embodiments of endoscopic treatment devices configured to ablate tissue at a controlled depth from within a body lumen by applying radio frequency spectrum energy, non-ionizing ultraviolet radiation, warm fluid or microwave radiation. U.S. Pat. No. 6,451,013 and related applications referenced therein describe devices for ablating tissue at a targeted depth from within a body lumen. Embodiments of laser-treatment elements are described for example in U.S. Pat. No. 4,887,605, among others. U.S. Pat. No. 6,589,235 teaches methods and device for cartilage reshaping by radiofrequency heating. U.S. Pat. No. 7,416,550 also teaches methods and devices for controlling and monitoring shape change in tissues, such as cartilage. The devices described in these and other patents and publications available to the skilled artisan may be adapted for use in treating portions of a Eustachian tube or surrounding tissues as described herein. U.S. Pat. Nos. 7,416,550, 6,589,235, 6,551,310, 6,451,013 and 4,887,605 are hereby incorporated by reference in their entireties.

In alternative embodiments, similar effects can be achieved through the use of energy removal devices, such as cryogenic therapies configured to transfer heat energy out of selected tissues, thereby lowering the temperature of targeted tissues until a desired level of tissue modification is achieved. Examples of suitable cryogenic therapy delivery elements are shown and described for example in U.S. Pat. Nos. 6,383,181 and 5,846,235, the entirety of each of which is hereby incorporated by reference.

In some embodiments, the treatment element 32 may be configured to deliver energy (e.g. heat, RF, ultrasound, microwave) or cryotherapy uniformly over an entire outer surface of the treatment element 32, thereby treating all tissues in contact with the treatment element 32. Alternatively, the treatment element 32 may be configured to deliver energy at only selective locations on the outer surface of the treatment element 32 in order to treat selected regions of tissues. In such embodiments, the treatment element 32 may be configured so that energy being delivered to selected regions of the treatment element can be individually controlled. In some embodiments, portions of the treatment element 32 are inert and do not deliver energy to the tissue. In further alternative embodiments, the treatment element 32 may be configured with energy-delivery (or removal) elements distributed over an entire outer surface of the treatment element 32. The control system 42 may be configured to engage such distributed elements individually or in selected groups so as to treat only targeted areas of the Eustachian tube or surrounding tissues.

In some embodiments, the treatment element 32 may be a balloon with energy delivery elements positioned at locations where energy transfer is sufficient or optimal to effect change in the Eustachian tube or its function or its surrounding tissues. Such a balloon may be configured to deliver energy while the balloon is in an inflated state, thereby providing a dual effect of repositioning tissue and delivering energy to effect a change. In other embodiments, a balloon may also deliver heat by circulating a fluid of elevated temperature though the balloon during treatment. The balloon can also delivery cryotherapy (e.g. by circulating a low-temperature liquid such as liquid nitrogen) while it is enlarged to alter the shape of a Eustachian tube or surrounding tissues.

Several embodiments may be employed for delivering energy treatment over a desired target area. For example, in some embodiments, a laser treatment system may treat a large surface area by scanning a desired treatment pattern over an area to be treated. In the case of microwave or ultrasound, suitably configured transducers may be positioned adjacent to a target area and desired transducer elements may be activated under suitable depth focus and power controls to treat a desired tissue depth and region. In some embodiments, ultrasound and/or microwave treatment devices may also make use of lenses or other beam shaping of focusing devices or controls. In some embodiments, one or more electrical resistance heating elements may be positioned adjacent to a target region, and activated at a desired power level for a therapeutically effective duration. In some embodiments, such heating elements may be operated in a cyclical fashion to repeatedly heat and cool a target tissue. In other embodiments, RF electrodes may be positioned adjacent to and in contact with a targeted tissue region. The RF electrodes may then be activated at some frequency and power level therapeutically effective duration. In some embodiments, the depth of treatment may be controlled by controlling a spacing between electrodes. In alternative embodiments, RF electrodes may include needles which may puncture tissue to a desired depth.

In some embodiments, the treatment element 32 and control system 42 may be configured to deliver treatment energy or cryotherapy to a selected tissue depth in order to target treatment at specific tissues. For example, in some embodiments, treatments may be targeted at tightening sections of the Eustachian tube or surrounding tissues. In other embodiments, treatments may be targeted at strengthening tissues of the soft palate to effect changes in the Eustachian tube and surrounding tissue. In further embodiments, treatments may be targeted at strengthening cartilage the area of the Eustachian tube. In still further embodiments, treatments may be targeted at stimulating or modifying the tissue of muscles of the ear, soft palate, nose, face, and/or head in order to modify the Eustachian tube.

In some embodiments, the treatment element 32 and control system 42 may be configured to deliver treatment energy to create specific localized tissue damage or ablation, stimulating the body's healing response to create desired conformational or structural changes in the Eustachian tube or surrounding tissues.

In some embodiments, the treatment element 32 and control system 42 may be configured to create specific localized tissue damage or ablation without the application of energy. For example the treatment element 32 may be configured to chemically cauterize tissue by delivering a cauterizing agent (e.g., silver nitrate, trichloroacetic acid, cantharidin, etc.) to the tissue. The treatment element 32 may include apertures configured to permit the cauterizing agent pass through to the target tissue. In some embodiments, the treatment element 32 may aerosolize the cauterizing agent. Other delivery methods are also contemplated. The treatment element 32 may include a lumen through which the cauterizing agent passes. The lumen may be fluidly connected to a reservoir or container holding the cauterizing agent. The device may include an input control (e.g., a button or switch) configured to control the delivery of the cauterizing agent. In some embodiments, the treatment element 32 includes an applicator that can be coated in a cauterizing agent (e.g., dipped in a reservoir of cauterizing agent, swabbed with cauterizing agent, etc.) and the coated treatment element applicator may be applied to tissue to be treated. In some embodiments, the treatment element may be configured to apply cauterizing agent to the patient over a prolonged period of time (e.g., 30 seconds, 1 minute, 2 minutes, etc.). In some embodiment, the treatment element 32 includes shields configured to protect tissue surrounding the tissue to be treated from coming into contact with the cauterizing agent. In some embodiments, a separate element is used to shield tissue surrounding the tissue to be treated from coming into contact with the cauterizing agent. While such treatments may be performed without the application of energy, in some embodiments, they are performed in conjunction with energy treatments.

In some embodiments, a treatment element may be configured to treat a patient's Eustachian tube or surrounding tissues by applying treatment (energy, cryotherapy, or other treatments) from a position outside the patient's face and head. In some embodiments, a device may be configured to apply energy from an element positioned externally to the patient, such as on the patient's skin. In another embodiment, a device may be placed on the external surface of the patient that would pull skin, muscle, or other tissue to effect a change in the Eustachian tube or surrounding tissues (e.g., a device for positioning the patient's jaw or ear). Treatment may then be applied to the Eustachian tube or surrounding tissues to achieve a desired Eustachian tube function.

In some embodiments, the device is configured to position tissue to be reshaped. In some embodiments, the device includes features and mechanisms to pull, push or position the tissue into a mold for reshaping. For example, suction, counter traction, or compression between two parts of the device may be used.

In some embodiments, the treatment device includes one, two, three, four, or more molds configured to reshape tissue. The mold or reshaping element may be fixed in size or may vary in size. The mold may also be fixed in shape or may vary in shape. For example, the size or shape of the element may be varied or adjusted to better conform to an airway of a patient. Adjustability may be accomplished using a variety of means, including, for example, mechanically moving the mold by way of joints, arms, guidewires, balloons, screws, stents, and scissoring arms, among other means. The mold may be adjusted manually or automatically. The mold is configured to impart a shape to the Eustachian tube or surrounding tissues area to improve actual or perceived Eustachian tube function.

In some embodiments, the mold or reshaping element includes a separate or integrated energy delivery or treatment element. The treatment element may be fixed or adjustable in size. For example, the treatment element may be adjusted to better conform to the tissue of a patient. In the case of a separate reshaping element and treatment element, a distance between the two elements may either be fixed or adjustable. Adjustability may be accomplished using a variety of means, including, for example, mechanically moving the mold by way of joints, arms, guidewires, balloons, screws, stents, and scissoring arms, among other means.

In some embodiments, the mold or another part of the device is configured to deliver cooling (discussed in more detail below). In some embodiments, the mold or reshaping element includes a balloon configured to reshape and/or deform tissue. A balloon may also be configured to deliver energy such as heat using hot liquid or gas.

Modifications to the foregoing system and method will be understood from the following additional example systems, methods, and devices for modifying a Eustachian tube.

Examples of Various Electrode Arrangements

Described below are embodiments of various treatment devices and, more particularly, electrode arrangements that may be used for applying energy to the Eustachian tube or surrounding tissues. These electrodes may, for example, deliver RF energy to preferentially shape the tissue to provide improved Eustachian tube function. In some embodiments, one or more electrodes may be used alone or in combination with a tissue shaping device or mold. In other embodiments, one or more electrodes may be integrally formed with a tissue shaping device or mold, so that the electrodes themselves create the shape for the tissue. In some embodiments, the energy delivery devices may utilize alternating current. In some embodiments, the energy delivery devices may utilize direct current. In certain such embodiments, the energy delivery device may include a configuration utilizing a grounding pad.

In some embodiments, the term "electrode" refers to any conductive or semi-conductive element that may be used to treat the tissue. This includes, but is not limited to metallic plates, needles, and various intermediate shapes such as dimpled plates, rods, domed plates, etc. Electrodes may also be configured to provide tissue deformation in addition to energy delivery. Unless specified otherwise, electrodes described can be monopolar (e.g., used in conjunction with a grounding pad) or bipolar (e.g., alternate polarities within the electrode body, used in conjunction with other tissue-applied electrodes).

In some embodiments, "mold", "tissue shaper", "reshaping element" and the like refer to any electrode or non-electrode surface or structure used to shape, configure or deflect tissue during treatment.

In some embodiments, "counter-traction" refers to applying a force opposite the electrode's primary force on the tissue to increase stability, adjustability, or for creating a specific shape.

In some embodiments, monopolar needles may be used to deliver energy. The needle electrodes 240 may be placed internally, penetrating through tissue to underlying tissue, and a remote grounding pad 242 or element may be placed externally. In some embodiments, monopolar needles may be used in conjunction with one or more molding elements which may be disposed on or around the needles. In some embodiments, monopolar transdermal needles may be used to deliver energy. In other embodiments (not shown), the needles may be placed external to the patient, and penetrate through to tissue to be treated. Needle configurations may advantageously target the particular tissue to be treated specifically. The monopolar transdermal needles may be used in conjunction with an internal molding device (not shown).

In some embodiments, bipolar needles may be used to deliver energy to tissue to be treated. The needles may be placed internally, with an insulating spacer between them and may penetrate through tissue to underlying tissue to be treated. In some embodiments, the bipolar needles may be used in combination with one or more internal molding elements. The one or more molding elements may be placed on or near the needles. In some embodiments, bipolar needles may be used to deliver energy. In other embodiments, the needles may be placed externally and penetrate through to tissue to be treated. Needle configurations may advantageously target particular tissue. The bipolar needles may be utilized in conjunction with an internal molding element.

Figure 4A:
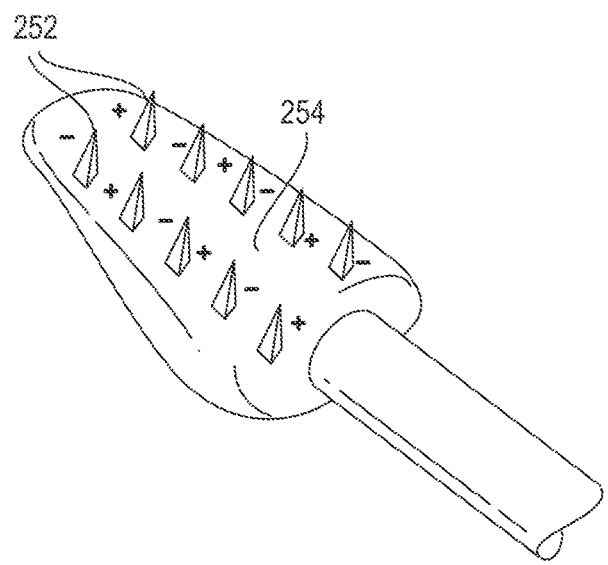
FIGS. 4A and 4B depict embodiments of various electrode arrangements for applying energy to tissue.

As shown in FIG. 4A, in some embodiments, an array of electrodes including one, two, or many pairs of bipolar needles 252 are located on a treatment element configured to be placed into contact with tissue. An insulator 254 may be disposed between the bipolar needles 252. An insulator may also be utilized on part of the needle's length to allow energy to be delivered only to certain tissue structures, such as cartilage or muscle. The electrodes may be placed internally or externally. The insulator 254 may also function as a mold or molding element. In some embodiments, the array of electrodes is used in conjunction with a separate tissue reshaping element.

Figure 4B:
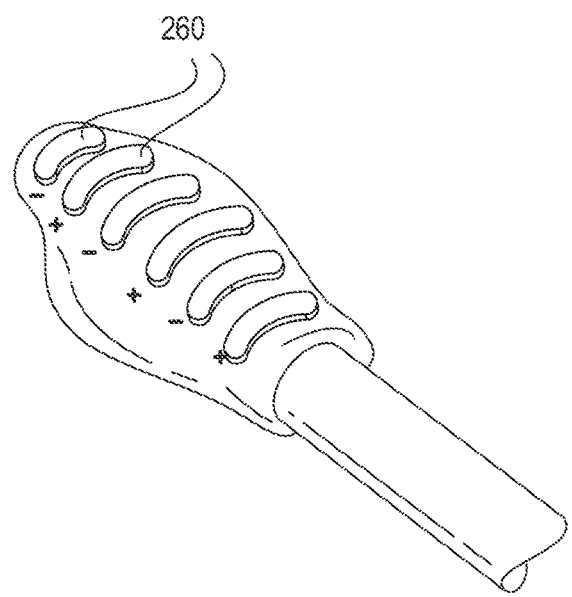

FIG. 4B illustrates another embodiment of a treatment element including one or more pairs of bipolar electrodes 260. As opposed to FIG. 4A, where the pairs of electrodes are arranged side-by-side, the embodiment of FIG. 4B arranges the pairs of electrodes along the length of the treatment element. The electrodes of FIG. 4B are also non-penetrating, in contrast to the needles of FIG. 4A. The electrodes 260 may, for example, be placed against the skin (externally) against internal tissue (e.g., mucosa) to deliver energy to target tissue such as cartilage or muscle.

In some embodiments of treatment devices including an array or multiple pairs of electrodes, each pair of electrodes (bipolar) or each electrode (monopolar) may have a separate, controlled electrical channel to allow for different regions of the treatment element to be activated separately. For example, the needles or needle pairs of FIG. 4A may be individually controlled to produce an optimal treatment effect. For another example, separate electrodes may be individually controlled to produce an optimal treatment effect. Other examples are also contemplated. The channels may include separate or integrated feedback. This may advantageously allow for more accurate temperature control and more precise targeting of tissue. Separate control may also allow energy to be focused and/or intensified on a desired region of the treatment element in cases where the anatomy of tissue and/or structures does not allow the entire electrode region of the treatment element to engage the tissue. In such embodiments, the tissue that is in contact with the treatment element may receive sufficient energy to treat the tissue.

Examples of Treatment Devices Including Electrodes

Figure 5A:
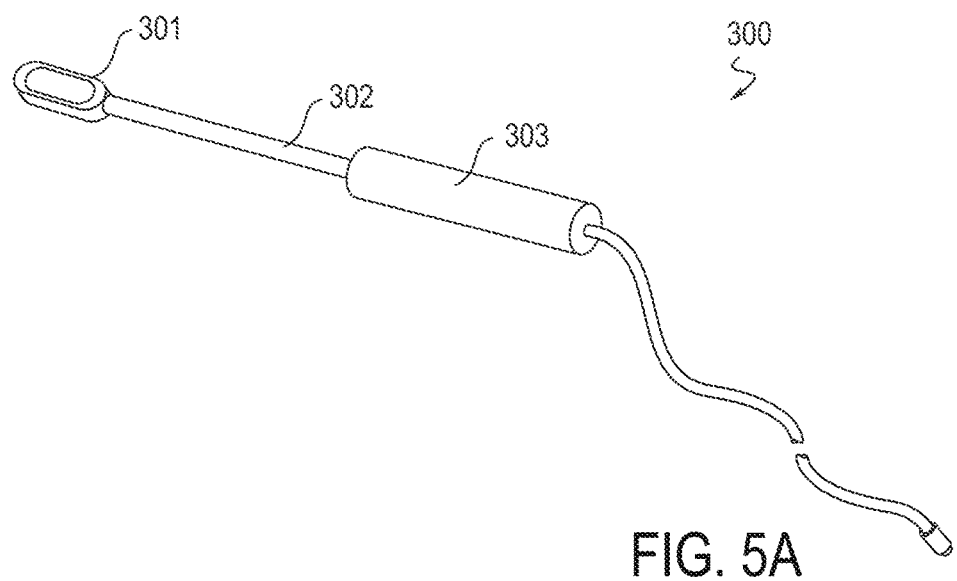
FIGS. 5A and 5B illustrate embodiments of devices for applying energy to tissue using a monopolar electrode.
Figure 5B:
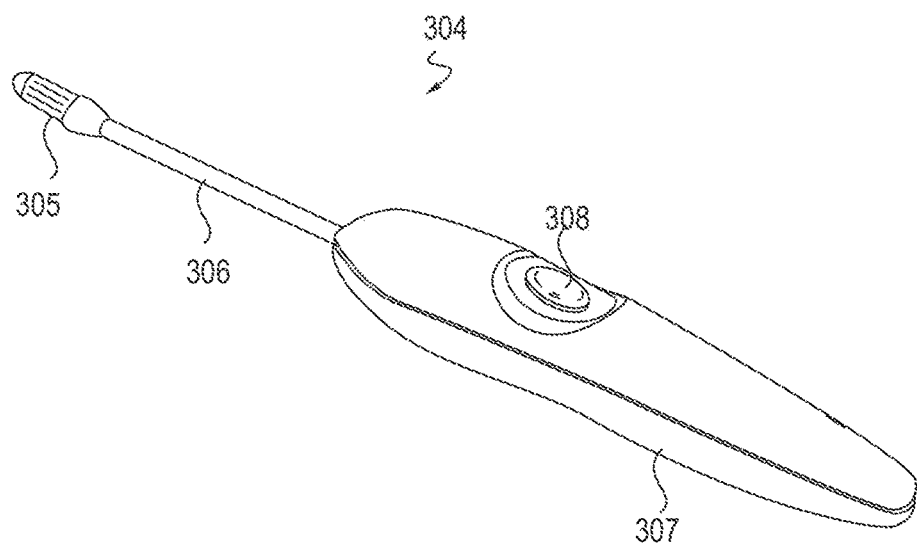

FIGS. 5A and 5B illustrate embodiments of treatment devices incorporating treatment elements such as electrodes. The instrument designs described in these embodiments may be used in a device such as the device 30, described above, and in the system of FIG. 3. In some embodiments, the devices provide tissue reshaping or molding in addition to energy delivery. Applying energy to the Eustachian tube or surrounding tissues may require properly positioning the electrode(s) at particular tissue, deflecting or deforming the tissue into a more functional shape, and delivering or applying energy consistently prior to device removal. Embodiments described herein may advantageously provide adjustability, visualization of effect, ease of use, ease of manufacturability and component cost. Molding and reshaping of the Eustachian tube or surrounding tissues may allow for non-surgical Eustachian tube improvement without the use of implants.

FIG. 5A depicts a device 300 including a single monopolar electrode 301 located at the end of a shaft 302. The shaft is attached to a handle 303 This embodiment may advantageously be simple to manufacture and may minimize current flow through, for example, the skin. In some embodiments, a monopolar electrode may be placed externally and may be connected to a molding element within the patient as well as a remote grounding pad. This embodiment may also advantageously be simple to manufacture, may minimize mucosal current flow, and may also be simple to position. In some embodiments, electrodes placed internally may be shaped to function as a mold or may include an additional structure that may function as a mold.

FIG. 5B depicts another device 304 including a single monopolar electrode 305. The electrode 305 is located at the distal end of a shaft 306, which is attached to a handle 307. The handle includes a power button 308 that may be used to activate and deactivate the electrode. As stated above, the device 304 may either include a generator or be connected to a remote generator. The electrode 305 may be provided on an enlarged, distal end of the shaft 306, and in the embodiment illustrated has a convex shape configured to press against and create a concavity in tissue.

Figure 6:
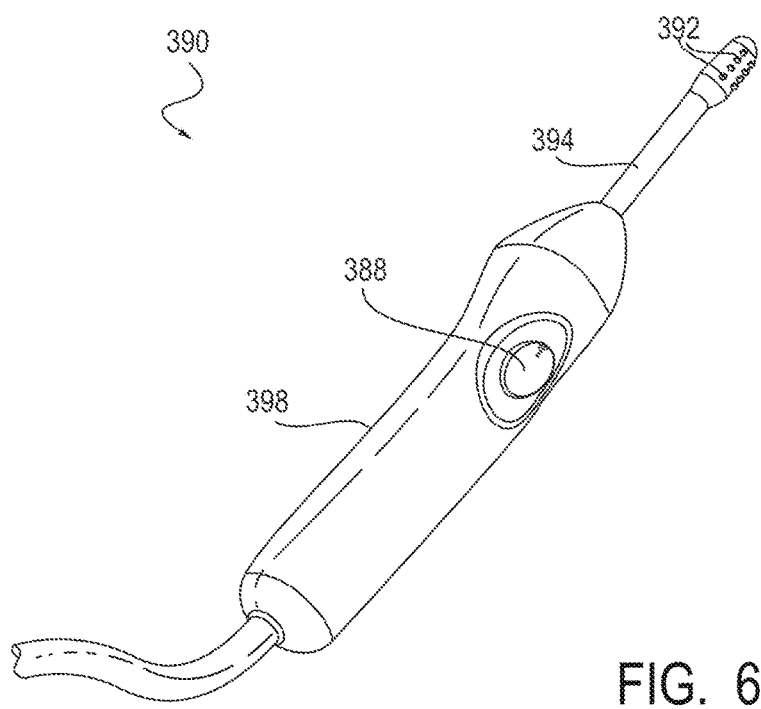
FIG. 6 shows an embodiment of a device for applying energy to tissue including an array of non-penetrating electrodes.

FIG. 6 depicts a device 390 including pairs of bipolar electrodes 392 located at the distal end of a shaft 394. The electrodes may be similar to the electrodes described with respect to the electrode configuration of FIG. 4B in that they are non-penetrating. The shaft 394 is connected to a handle 398 which includes a button configured to activate and deactivate the electrodes. As stated above, the device 380 may either include a generator or be connected to a remote generator.

Figure 7A:
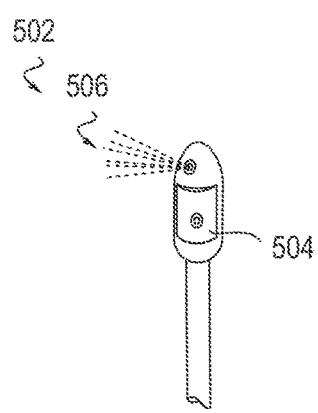
FIGS. 7A and 7B illustrate an embodiment of a device for applying energy to tissue.
Figure 7B:
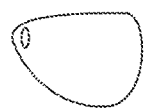

FIG. 7A depicts the treatment element 502 of a treatment device (e.g., device 30). The treatment element 502 of the device includes a monopolar electrode 504. A cross-section of the treatment element 502 is shown in FIG. 7B. It includes an asymmetrical shape and has a convex surface where the electrode is positioned configured to conform to tissue. The treatment element 502 further includes a light 506 configured to illuminate the treatment area. For example an LED or a visible laser may be used. The visible laser may experience less diffusion in the tissue. Furthermore, the light 506 can be situated such that light can be transmitted through the tissue (including the skin) and can be visualized externally by the user (e.g., during a procedure). The user can then use the light to properly position the device in the desired location.

Figure 8A:
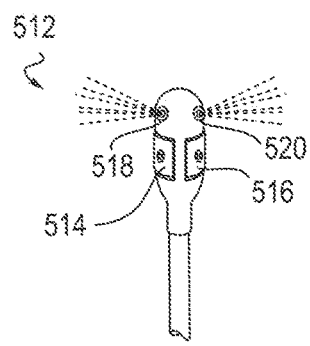
FIGS. 8A and 8B illustrate an embodiment of a device for applying energy to tissue.
Figure 8B:

FIG. 8A depicts the treatment element 512 of a treatment device (e.g., device 30). The treatment element 512 of the device includes two monopolar electrodes 514, 516 provided side-by-side on a convex surface of the treatment element. The cross section of the treatment element 512 may be configured to conform to the shape of particular tissue. Each electrode may be activated separately, simultaneously, and/or in an alternating fashion. The treatment element 512 also includes two lights 518, 520 (e.g., LEDs, lasers) configured to illuminate the treatment area. One or both of the lights 518, 520 can also be situated such that light can be transmitted through the skin and can be visualized externally by the user. The user can then use the light to properly position the device in the desired location.

FIG. 9A depicts a treatment element 522 of a treatment device (e.g., device 30). The tip 522 of the device includes a monopolar electrode 524. The tip 522 includes a symmetrical cross-section as shown in FIG. 9B. The tip 522 includes a light 526 (e.g., LED) configured to illuminate the treatment area. The light 526 can also be situated such that light can be transmitted through the skin and can be visualized externally by the user. The user can use the light to properly position the device in the desired location.

Figure 10B:
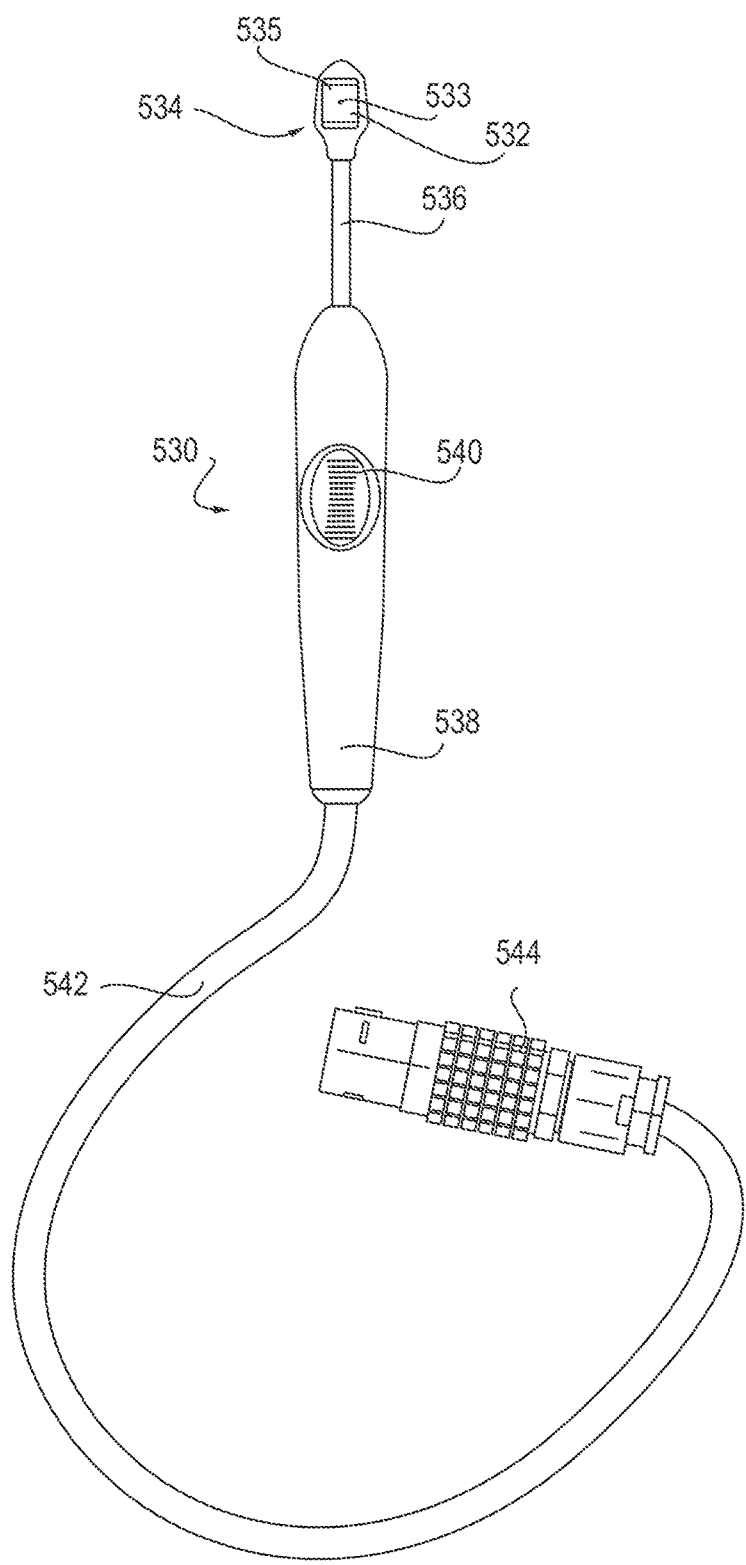

FIGS. 10A-G depict a treatment device 530 similar to the embodiments of FIGS. 5A, and 5B. FIGS. 10A and 10F provide perspective views of the device 530. The device 530 includes a treatment element 532 at its distal tip 534. The treatment element 532 includes an electrode 535. The body of the treatment element 532, itself, may include an insulating material. The treatment element 532 may be provided on an enlarged distal tip 534 of an elongate shaft 536, and as in the embodiment illustrated, may have a convex shape configured to press against and create a concavity in tissue. The distal tip 534 is located at the distal end of shaft 536. The shaft is attached at its proximal end to a handle 538. The handle 538 includes an input control such as a power button 540 on its front side that may be used to activate and deactivate the electrode. The power button 540 may be positioned in a recess of the handle to allow for finger stability when activating and deactivating the electrode. In other embodiments, the input control is in the form of a switch or dial. Other configurations are also possible as described above.

The device 530 includes a flexible wire or cable 542 electrically connected to an adaptor 544. The adaptor 544 can be used to connect the device 530 to a remote generator (not shown). The adaptor 544 may allow transmission of treatment energy between a remote generator and the device 530. The adaptor may also allow transmission of any sensor signals between the device 530 and a generator or control unit. The device 530 may either include an integrated generator or be connected to a remote generator. The treatment device 530 may be provided in a system or kit also including the remote generator. The system or kit (with or without the remote generator) may also include a grounding device and/or a cooling device as described above and further below. In some embodiments, the kit may include a positioning element configured to help a user locate the optimal treatment area.

Figure 10C:
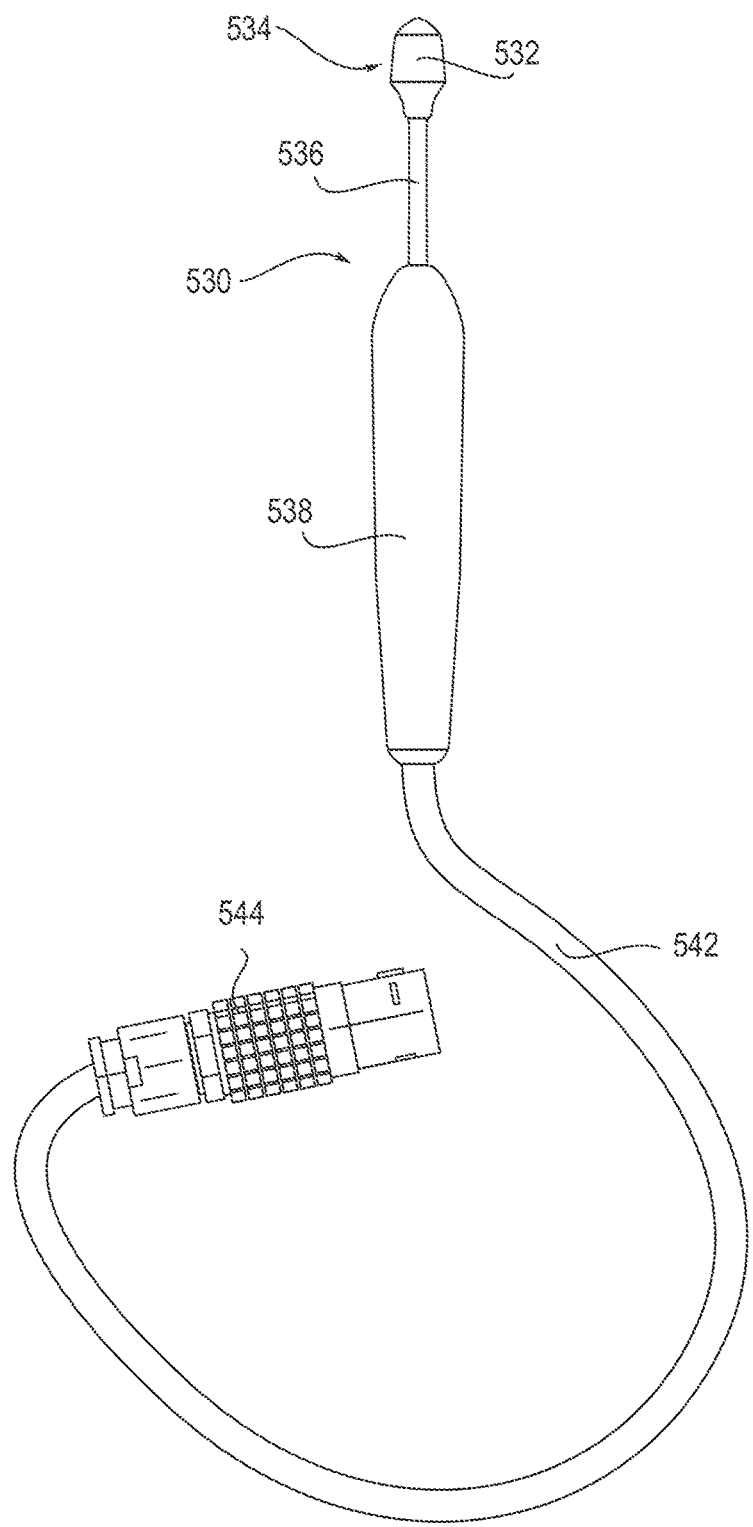

FIGS. 10B and 10C depict front and back views of the device. As shown in FIGS. 10B and 10C, the handle 538 of the device generally as a rounded elongate shape. Other shapes are also possible. For example the device 530 may have a square shaped cross section. In some embodiments, a circumference (or width or cross-sectional area) of the handle 538 may increase distally along the length of the handle 538.

Figure 10D:
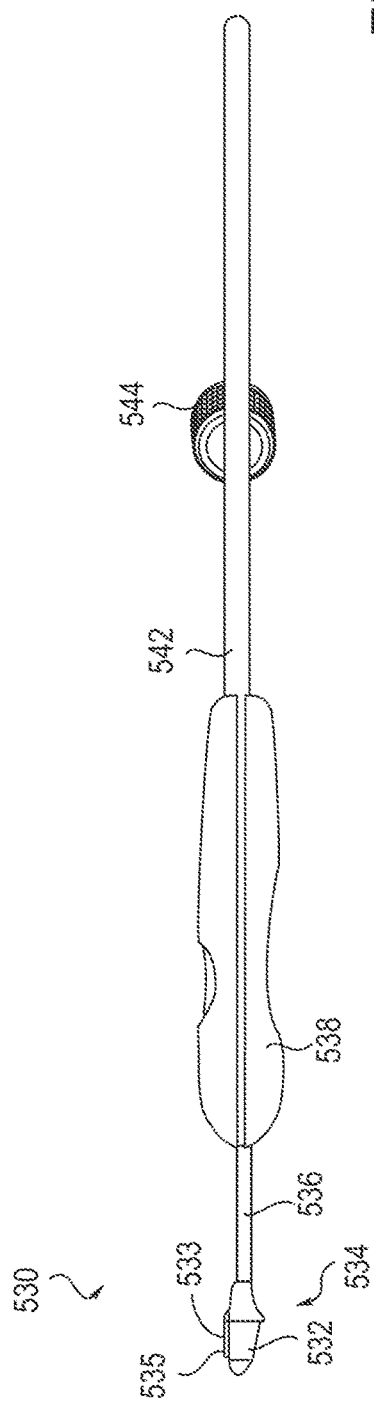
Figure 10E:
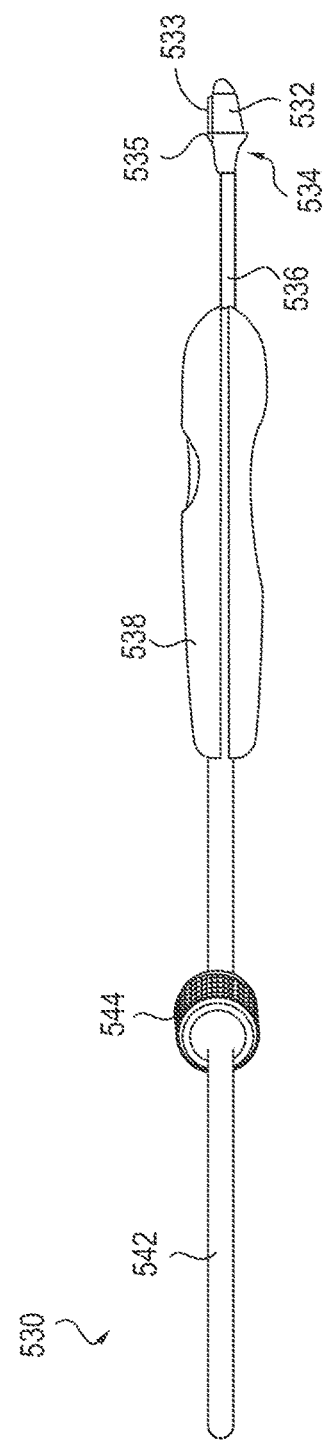

FIGS. 10D and 10E depict side views of the device. As shown in FIGS. 10D and 10E, the handle 538 of the device 530 may include an indentation or recess around the middle of the handle 538. This may allow for enhanced grip and control when a user is holding the device. The indentation or recess may be near the input control or power button 540 to allow a user to easily activate and deactivate the device while holding it in a comfortable position.

In some embodiments, the shaft has a width or diameter of about 0.125 inches to about 0.25 inches. In some embodiments, the shaft is about 1.5 inches to about 4 inches long. In some embodiments, the shaft includes a polymer such as polycarbonate or PEEK. In other embodiments, the shaft includes stainless steel or other metals. The metals may be coated with an external and/or internal insulating coating (e.g., polyester, polyolefin, etc.). The handle may include the same material as the shaft, in some embodiments. In some embodiments, the shaft is rigid. This may allow a user of the device increased control over the deformation of nasal tissue. In some embodiments, the shaft comprises some amount of flexibility. This flexibility may allow a user adjust an angle of the distal tip by bending the distal end of the shaft.

FIG. 10G depicts a larger view of the distal tip 534 of the device 530. As shown best in FIG. 10G, the treatment element 532 includes a generally elongate shape. The front of the treatment element 532 includes a shallow, curved surface, providing a convex shape configured to deform the nasal tissue and create a concavity therein. In some embodiments, the front of the treatment element includes a concave shape. The shape of the front surface of the treatment element may be selected to conform to the nasal tissue. The back of the treatment element 532 also includes a shallow curved surface. As best seen in FIGS. 10D and 10E, the back surface varies in width along the length of the back surface of the treatment element 532. The back surface widens, moving distally along the tip until it is nearly in line with the proximal end of the electrode plate 535. The back surface then narrows towards the distal tip of the treatment element 532. This shape may maximize visualization of the area to be treated, while, at the same time, providing sufficient rigidity for treatment. Other shapes are also possible. For example, the treatment element may include a generally spherical or cylindrical shape. In some embodiments, the treatment element includes an angular shape (e.g., triangular, conical) which may allow for close conformation to the tissue structures. The treatment element 532 includes a monopolar electrode plate 535. The monopolar electrode plate 535 can be in the shape of a rectangle having a curved or convex tissue-facing surface. Other shapes are also possible (e.g., square, circular, ovular, etc.). The electrode 535 may protrude slightly from the treatment element 535. This may allow the electrode to itself provide a convex shape configured to create a concavity in tissue to be treated.

In some embodiments, the treatment element has a width or diameter of about 0.25 inches to about 0.45 inches. In some embodiments, the treatment element is about 0.4 inches to about 0.5 inches long. The treatment element can, in some embodiments, include a ceramic material (e.g., zirconium, alumina, silicon glass). Such ceramics may advantageously possess high dielectric strength and high temperature resistance. In some embodiments, the treatment element includes polyimides or polyamides which may advantageously possess good dielectric strength and elasticity and be easy to manufacture. In some embodiments, the treatment element includes thermoplastic polymers. Thermoplastic polymers may advantageously provide good dielectric strength and high elasticity. In some embodiments, the treatment element includes thermoset polymers, which may advantageously provide good dielectric strength and good elasticity. In some embodiments, the treatment element includes glass or ceramic infused polymers. Such polymers may advantageously provide good strength, good elasticity, and good dielectric strength.

In some embodiments, the electrode has a width of about 0.15 inches to about 0.25 inches. In some embodiments, the electrode is about 0.2 inches to about 0.5 inches long. In some embodiments, the treatment element includes steel (e.g., stainless, carbon, alloy). Steel may advantageously provide high strength while being low in cost and minimally reactive. In some embodiments, the electrodes or energy delivery elements described herein include materials such as platinum, gold, or silver. Such materials may advantageously provide high conductivity while being minimally reactive. In some embodiments, the electrodes or energy delivery elements described herein include anodized aluminum. Anodized aluminum may advantageously be highly stiff and low in cost. In some embodiments, the electrodes or energy delivery elements described herein include titanium which may advantageously possess a high strength to weight ratio and be highly biocompatible. In some embodiments, the electrodes or energy delivery elements described herein include nickel titanium alloys. These alloys may advantageously provide high elasticity and be biocompatible. Other similar materials are also possible.

As shown in the embodiment of FIG. 10G, the treatment element 532 further includes a pin-shaped structure including a thermocouple 533 within an insulating bushing extending through a middle portion of the plate 535. In some embodiments, different heat sensors (e.g., thermistors) may be used. In some embodiments, the thermocouple 533 is configured to measure a temperature of the surface or subsurface of tissue to be treated or tissue near the tissue to be treated. A pin-shape having a sharp point may allow the structure to penetrate the tissue to obtain temperature readings from below the surface. The thermocouple can also be configured to measure a temperature of the treatment element 532 itself. The temperature measurements taken by the thermocouple can be routed as feedback signals to a control unit (e.g., the control system 42 described with respect to FIG. 3) and the control unit can use the temperature measurements to adjust the intensity of energy being delivered through the electrode. In some embodiments, thermocouples or other sensing devices may be used to measure multiple tissue and device parameters. For example, multiple thermocouples or thermistors may be used to measure a temperature at different locations along the treatment element. In some embodiments, one of the sensors may be configured to penetrate deeper into the tissue to take a measurement of a more interior section of tissue. For example, a device may have multiple sensors configured to measure a temperature at the Eustachian tube, surrounding tissue, and/or the treatment element itself. As described above, in some embodiments, the sensors described herein are configured to take a measurement of a different parameter. For example, tissue impedance can be measured. These measurements can be used to adjust the intensity and/or duration of energy being delivered through the treatment element. This type of feedback may be useful from both an efficacy and a safety perspective.

As shown in FIG. 10G, in some embodiments the thermocouple is within a pin shaped protrusion on the surface of the electrode 535. In other embodiments, the thermocouple can simply be on the surface of the electrode. In other embodiments, the thermocouple can protrude from the surface of the electrode in a rounded fashion. Rounded structures may be pressed into the tissue to obtain subsurface temperature readings. Other configurations and locations for the thermocouple are also possible. The use of thermocouples or temperature sensors may be applied not only to the embodiment of FIG. 10G, but also to any of the other embodiments described herein.

Figure 11A:
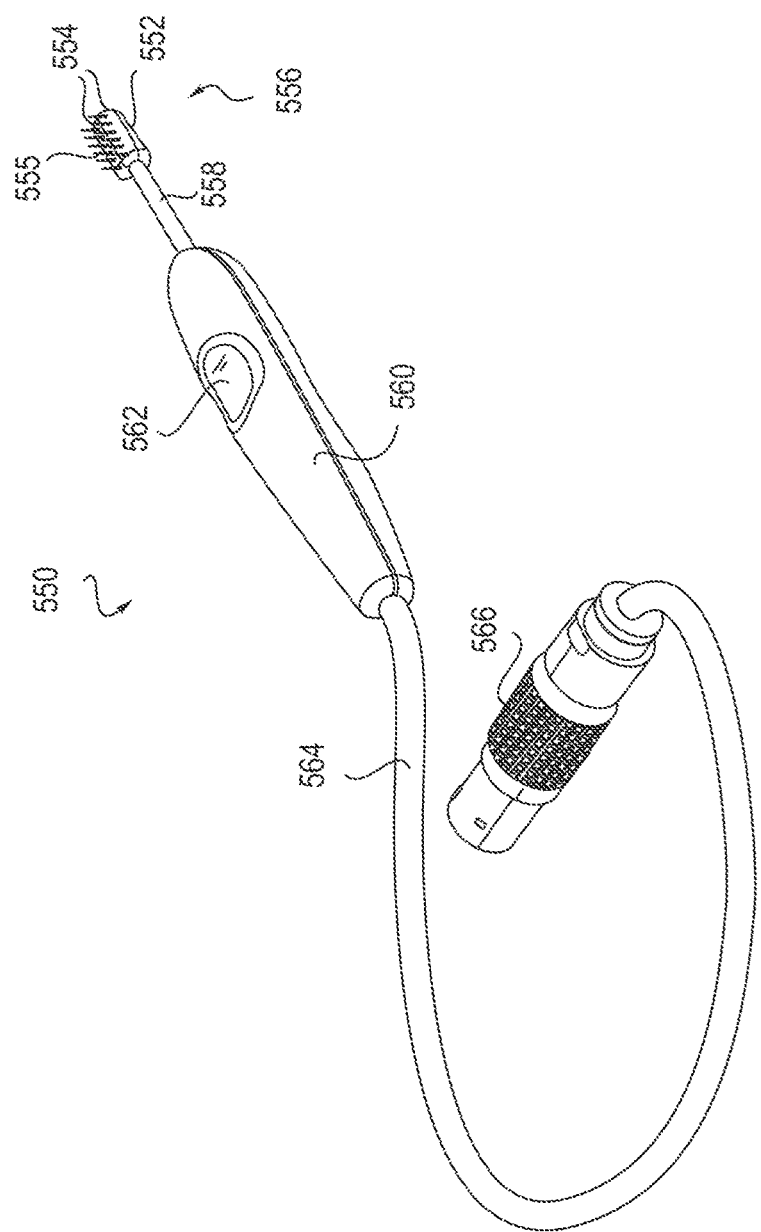
FIGS. 11A-11G illustrate an embodiment of a device for applying energy to tissue using an array of needle electrodes.
Figure 11B:
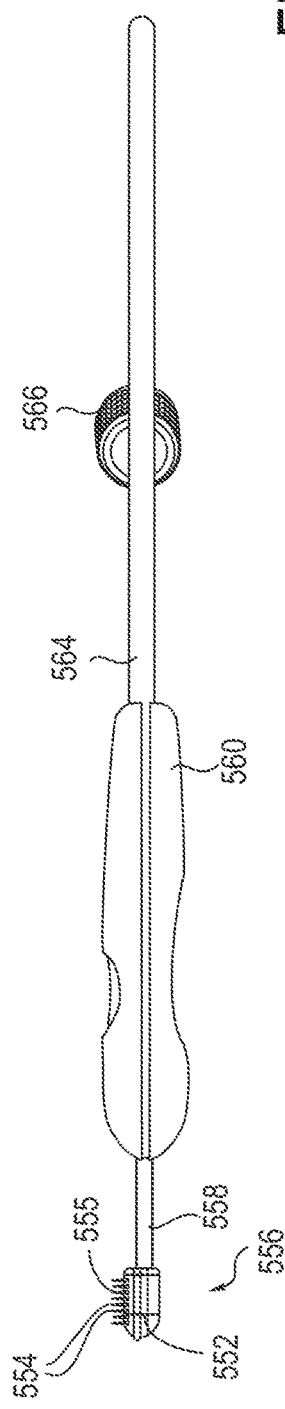
Figure 11C:
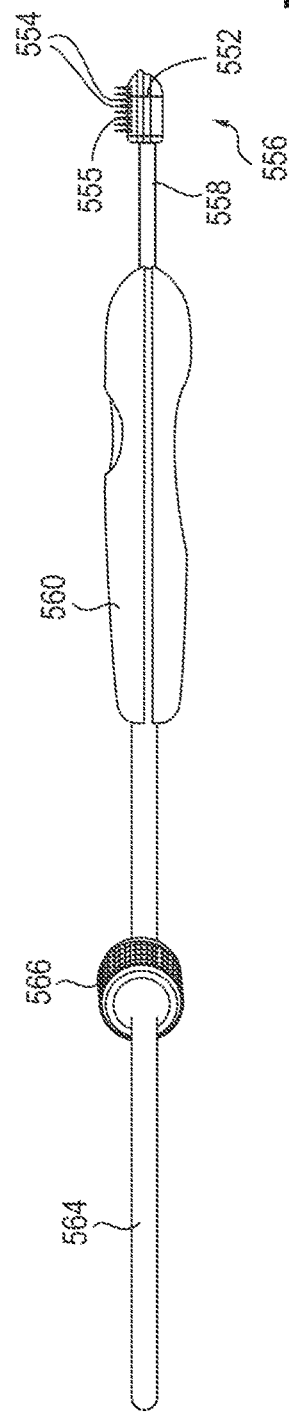
Figure 11D:
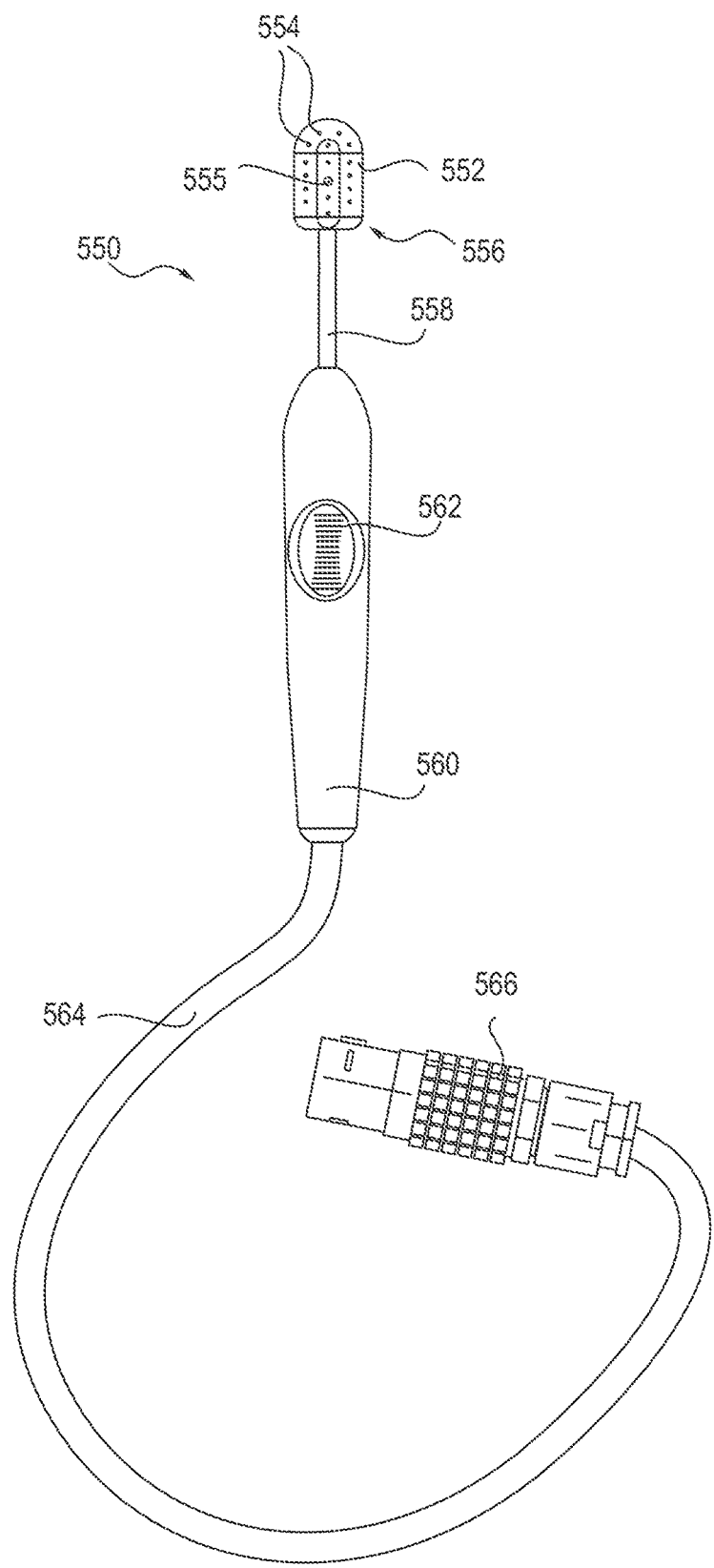
Figure 11E:
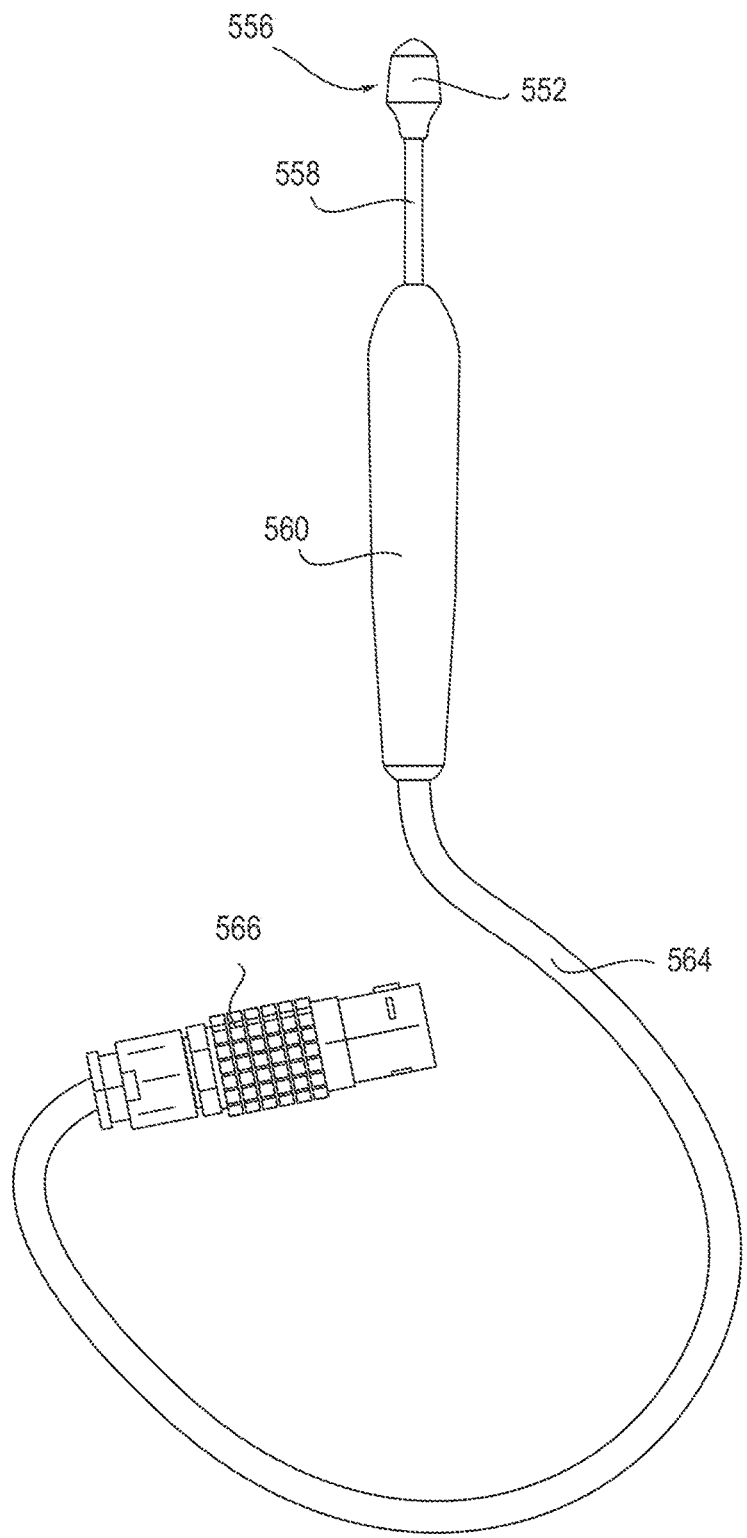
Figure 11F:
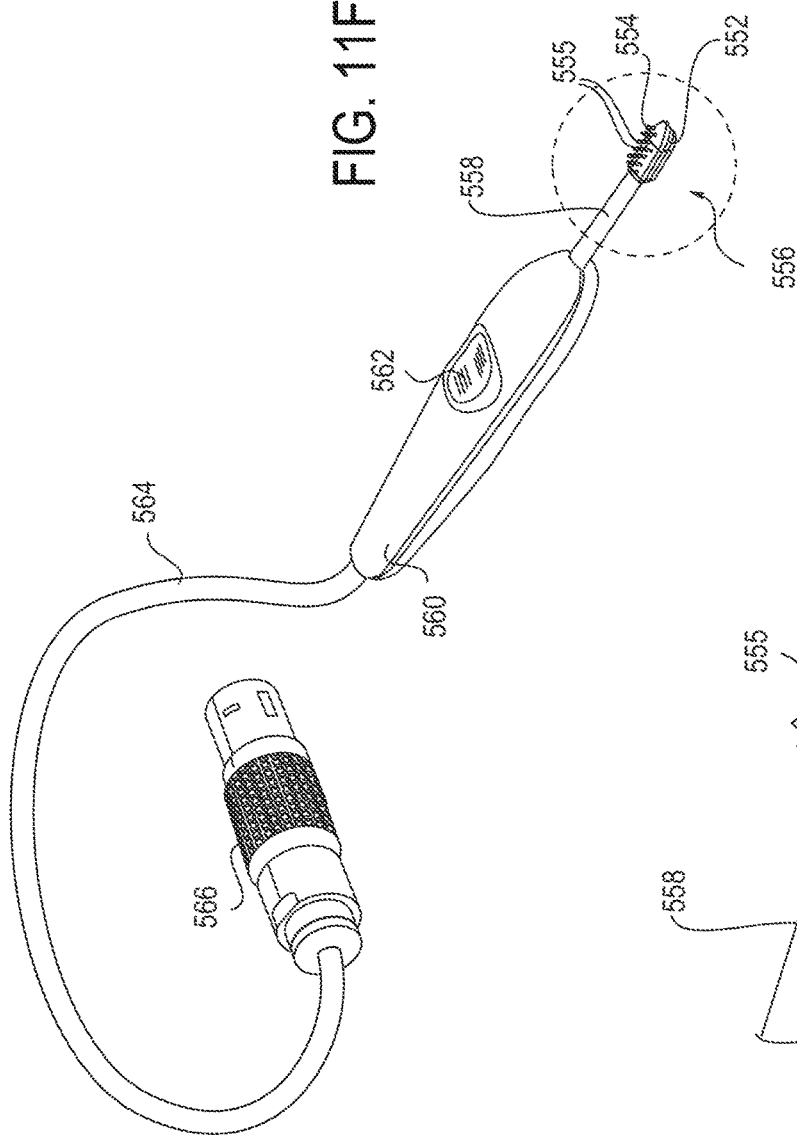

FIGS. 11A-G depict a treatment device 550 similar to the embodiment of FIG. 4A. FIGS. 11A and 11F are perspective views of the device 550 and show the device 550 including a treatment element 552 at the distal tip 556 of the device 550. The treatment element 552 may be provided on an enlarged distal tip 556 of an elongate shaft 558, and as in the embodiment illustrated, may have a convex shape configured to press against and create a concavity in tissue. The distal tip 556 is located at a distal end of shaft 558. The shaft is attached at its proximal end to a handle 560. The handle 560 includes an input control, such as a power button 562, on its front side that may be used to activate and deactivate the electrode. The power button may be positioned in a recess of the handle to allow for finger stability when activating and deactivating the electrode. In other embodiments, the input control is in the form of a switch or dial. Other configurations are also possible as described above. The device 550 may either include a generator or be connected to a remote generator. The device 550 may include a flexible wire or cable 564 that connects to an adaptor 566 that is configured to be plugged into a remote generator (not shown). The adaptor 566 may allow transmission of treatment energy between a remote generator and the device 550. The adaptor 566 may also allow transmission of any sensor signals between the device 550 and a generator or control unit. The treatment device 550 may be provided in a system or kit also including the remote generator. The system or kit (with or without the remote generator) may also include a grounding device and/or a cooling device as described above and further below. In some embodiments, the kit includes a positioning element configured to help a user locate the optimal treatment area.

In some embodiments, the shaft has a width or diameter or about 0.235 inches to about 0.25 inches. In some embodiments, the shaft is about 1.5 inches to about 4 inches long. In some embodiments, the shaft and/or handle includes a polymer such as polycarbonate or PEEK. In other embodiments, the shaft includes stainless steel or other metals. The metals may be coated with an external and/or internal insulating coating (e.g., polyester, polyolefin, etc.). The handle may include the same material as the shaft, in some embodiments. In some embodiments, the shaft is rigid. This may allow a user of the device increased control over the deformation of nasal tissue. In some embodiments, the shaft includes some amount of flexibility. This flexibility may allow a user adjust an angle of the distal tip by bending the distal end of the shaft.

FIGS. 11B and 11C depict side views of the device. As shown in FIGS. 11B and 11C, the handle 560 of the device 550 may include an indentation or recess around the middle of the handle 560. This may allow for enhanced grip and control when a user is holding the device. The indentation or recess may be near the input control or power button 562 to allow a user to easily activate and deactivate the device while holding it in a comfortable position.

FIGS. 11D and 11E depict front and back views of the device. As shown in FIGS. 11D and 11E, the handle 560 of the device generally includes a rounded elongate shape. Other shapes are also possible. For example the device 550 may have a square shaped cross section. In some embodiments, a circumference (or width or cross-sectional area) of the handle 560 may increase distally along the length of the handle 560.

Figure 11G:
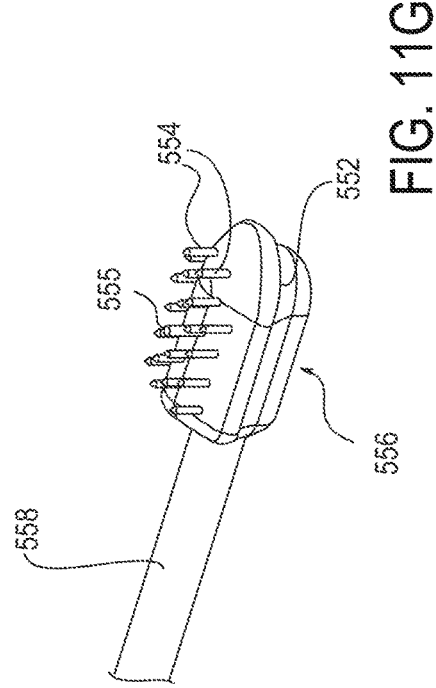

FIG. 11G depicts a larger view of the distal tip 556 of the device 550. As shown best in FIG. 11G, the treatment element 552 includes a generally elongate shape. The front of the treatment element 552 includes a shallow curved surface, providing a convex shape configured to deform the tissue and create a concavity therein. In some embodiments, the front of the treatment element includes a concave shape. The shape of the front surface of the treatment element may be selected to conform to tissue. The back surface of the treatment element 552 includes a shallow curved surface along most of its length. As best seen in FIGS. 11B and 11C, the back surface narrows distally along the length of the element 552 from approximately the distal end of the needle electrodes to the distal tip of the treatment element 552. This shape may maximize visualization of the area to be treated, while, at the same time, providing sufficient rigidity for treatment. Other shapes are also possible. For example, the treatment element may include a generally spherical or cylindrical shape. In some embodiments, the treatment element includes an angular shape (e.g., triangular, conical) which may allow for close conformation to the tissue structures. The treatment element 552 includes a monopolar or bipolar needle array including multiple needles 554. In some embodiments, the needles 554 are energized in between select needles to deliver bipolar energy. In other embodiments, the energy is delivered between the needles 554 and a remote grounding pad (not shown). In some embodiments, the electrode needle pairs are arranged horizontally across the treatment element 552. In some embodiments, the electrode needle pairs are arranged vertically across the treatment element 552, or along the direction of the shaft 558 and handle 560. Other configurations are also possible. For example, the needle pairs may be arranged diagonally across the treatment element 552. The treatment element 552 may be placed either internally or the treatment element 552 may be placed externally. The distal tip 556 of the device 550 may also function as a mold or molding element. In a monopolar embodiment, the energy may be selectively delivered between certain sets of needles, all needles, or even individual needles to optimize the treatment effect.

The treatment element 552 of the device 550 further includes a pin-shaped structure including a thermocouple 555 within an insulating bushing extending through a middle portion of the front surface of the treatment element 552. In some embodiments, different heat sensors (e.g., thermistors) may be used. As described above, in some embodiments, the thermocouple 555 is configured to measure a temperature of the surface or subsurface of tissue to be treated or tissue near the tissue to be treated. A pin-shape having a sharp point may allow the structure to penetrate the tissue to obtain temperature readings from below the surface. The thermocouple can also be configured to measure a temperature of the treatment element 552 itself. The temperature measurements taken by the thermocouple can be routed as feedback signals to a control unit (e.g., the control system 42 described with respect to FIG. 3) and the control unit can use the temperature measurements to adjust the intensity of energy being delivered through the electrode. In some embodiments, thermocouples or other sensing devices may be used to measure multiple tissue and device parameters. For example, multiple thermocouples or thermistors may be used to measure a temperature at different locations along the treatment element. In some embodiments, one of the sensors may be configured to penetrate deeper into the tissue to take a measurement of a more interior section of tissue. For example, a device may have multiple sensors configured to measure a temperature at the mucosa, the cartilage, and/or the treatment element itself. As described above, in some embodiments, the sensors described herein are configured to take a measurement of a different parameter. For example, tissue impedance can be measured. These measurements can be used to adjust the intensity and/or duration of energy being delivered through the treatment element. This type of feedback may be useful from both an efficacy and a safety perspective.

In some embodiments, the treatment element has a width or diameter of about 0.25 inches to about 0.45 inches. In some embodiments, the treatment element is about 0.4 inches to about 0.5 inches long. The treatment element can, in some embodiments, include a ceramic material (e.g., zirconium, alumina, silicon glass). Such ceramics may advantageously possess high dielectric strength and high temperature resistance. In some embodiments, the treatment element includes polyimides or polyamides which may advantageously possess good dielectric strength and elasticity and be easy to manufacture. In some embodiments, the treatment element includes thermoplastic polymers. Thermoplastic polymers may advantageously provide good dielectric strength and high elasticity. In some embodiments, the treatment element includes thermoset polymers, which may advantageously provide good dielectric strength and good elasticity. In some embodiments, the treatment element includes glass or ceramic infused polymers. Such polymers may advantageously provide good strength, good elasticity, and good dielectric strength.

In some embodiments, the electrodes have a width or diameter of about 0.15 inches to about 0.25 inches. In some embodiments, the electrode is about 0.2 inches to about 0.5 inches long. In some embodiments, the treatment element includes steel (e.g., stainless, carbon, alloy). Steel may advantageously provide high strength while being low in cost and minimally reactive. In some embodiments, the electrodes or energy delivery elements described herein include materials such as platinum, gold, or silver. Such materials may advantageously provide high conductivity while being minimally reactive. In some embodiments, the electrodes or energy delivery elements described herein include anodized aluminum. Anodized aluminum may advantageously be highly stiff and low in cost. In some embodiments, the electrodes or energy delivery elements described herein include titanium which may advantageously possess a high strength to weight ratio and be highly biocompatible. In some embodiments, the electrodes or energy delivery elements described herein include nickel titanium alloys. These alloys may advantageously provide high elasticity and be biocompatible. Other similar materials are also possible.

Energy applied to the tissue to be treated using any combination of the embodiments described in this application may be controlled by a variety of methods. In some embodiments, temperature or a combination of temperature and time may be used to control the amount of energy applied to the tissue. Tissue is particularly sensitive to temperature; so providing just enough energy to reach the target tissue may provide a specific tissue effect while minimizing damage resulting from energy causing excessive temperature readings. For example, a maximum temperature may be used to control the energy. In some embodiments, time at a specified maximum temperature may be used to control the energy. In some embodiments, thermocouples, such as those described above, are provided to monitor the temperature at the electrode and provide feedback to a control unit (e.g., control system 42 described with respect to FIG. 3). In some embodiments, tissue impedance may be used to control the energy. Impedance of tissue changes as it is affected by energy delivery. By determining the impedance reached when a tissue effect has been achieved, a maximum tissue impedance can be used to control energy applied.

In the embodiments described herein, energy may be produced and controlled via a generator that is either integrated into the electrode handpiece or as part of a separate assembly that delivers energy or control signals to the handpiece via a cable or other connection. In some embodiments, the generator is an RF energy source configured to communicate RF energy to the treatment element. For example, the generator may include a 460 KHz sinusoid wave generator. In some embodiments, the generator is configured to run between about 1 and 100 watts. In some embodiments, the generator is configured to run between about 5 and about 75 watts. In some embodiments, the generator is configured to run between about 10 and 50 watts.

In some embodiments, the energy delivery element includes a monopolar electrode (e.g., electrode 535 of FIG. 10G). Monopolar electrodes are used in conjunction with a grounding pad. The grounding pad may be a rectangular, flat, metal pad. Other shapes are also possible. The grounding pad may include wires configured to electrically connect the grounding pad to an energy source (e.g., an RF energy source).

In some embodiments, the energy delivery element such as the electrodes described above can be flat. Other shapes are also possible. For example, the energy delivery element can be curved or include a complex shape. For example, a curved shape may be used to place pressure or deform the tissue to be treated. The energy delivery element may include needles or microneedles. The needles or microneedles may be partially or fully insulated. Such needles or microneedles may be configured to deliver energy or heat to specific tissues while avoiding tissues that should not receive energy delivery.

In some embodiments, the electrodes or energy delivery elements described herein include steel (e.g., stainless, carbon, alloy). Steel may advantageously provide high strength while being low in cost and minimally reactive. In some embodiments, the electrodes or energy delivery elements described herein include materials such as platinum, gold, or silver. Such materials may advantageously provide high conductivity while being minimally reactive. In some embodiments, the electrodes or energy delivery elements described herein include anodized aluminum. Anodized aluminum may advantageously be highly stiff and low in cost. In some embodiments, the electrodes or energy delivery elements described herein include titanium which may advantageously possess a high strength to weight ratio and be highly biocompatible. In some embodiments, the electrodes or energy delivery elements described herein include nickel titanium alloys. These alloys may advantageously provide high elasticity and be biocompatible. Other similar materials are also possible.

In some embodiments, the treatment elements (e.g., non-electrode portion of treatment element) of the devices described herein include an insulating material such as a ceramic material (e.g., zirconium, alumina, silicon glass). In some embodiments, the treatment elements include an insulating material interposed between multiple electrodes or electrode section. These insulating sections may provide an inert portion of the treatment element that does not delivery energy to the tissue. Such ceramics may advantageously possess high dielectric strength and high temperature resistance. In some embodiments, the insulators described herein include polyimides or polyamides which may advantageously possess good dielectric strength and elasticity and be easy to manufacture. In some embodiments, the insulators described herein include thermoplastic polymers. Thermoplastic polymers may advantageously provide good dielectric strength and high elasticity. In some embodiments, the insulators described herein include thermoset polymers, which may advantageously provide good dielectric strength and good elasticity. In some embodiments, the insulators described herein include glass or ceramic infused polymers. Such polymers may advantageously provide good strength, good elasticity, and good dielectric strength.

In some embodiments, the handle and/or shaft of the devices include the same materials as those described with respect to the insulators. In some embodiments, the handle and/or shaft of the device includes a metal, such as stainless steel. In other embodiments, the handle and/or shaft of the device includes a polymer, such as polycarbonate. Other metals and polymers are also contemplated.

In some embodiments, the device may be used in conjunction with a positioning element that can be used to aid in positioning of the device. The positioning element may be integrated into the device itself or can be separate. The positioning element may be used to determine the optimal placement of the device to achieve maximal increase in efficacy.

In some embodiments, a positioning element includes a shaft including measurement marks indicating depth. For example, a physician may insert this element into an airway of the patient to find an appropriate treatment depth of treatment. The positioning element may include marks around the base of the shaft and/or along the length of the shaft indicating rotation and depth, respectively. The positioning element may also include marks indicating angle of insertion. The physician may then use the measurement marks to guide insertion of the treatment element to a particular spot.

It will be appreciated that any combination of electrode configurations, molds, handles, connection between handles, and the like may be used to treat the Eustachian tube and/or surrounding tissues.

Cooling Systems

Embodiments of devices configured to heat specific tissue while maintaining lower temperatures in other adjacent tissue are provided. These devices may be incorporated into any of the treatment apparatuses and methods described herein. The Eustachian tube and surrounding tissue is an example of tissue that may benefit from being maintained at different temperatures. Other examples include the skin, which includes the epidermis, dermis, and subcutaneous fat, the tonsils, which include mucosa, glandular tissue, and vessels. Treatment of other tissue complexes is also possible. For example, in some embodiments, the internal structures of a patient's head may be heated while maintaining a lower temperature in mucosal lining of the nasopharynx and/or skin. In other embodiments, mucosa, skin, or other tissue may be heated, while maintaining lower temperatures elsewhere. Limiting unwanted heating of non-target tissues may allow trauma and pain to be reduced, may reduce scarring, may preserve tissue function, and may also decrease healing time. Combinations of heat transfer and/or heat isolation may allow directed treatment of specific tissue such as cartilage or muscle, while excluding another tissue, such as mucosa, without surgical dissection.

Figure 12A:
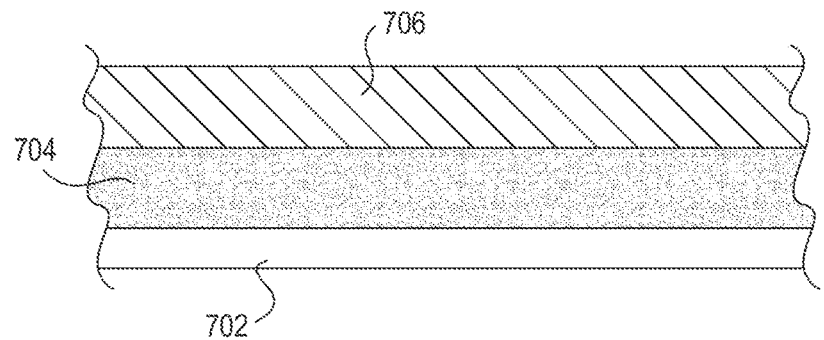
FIG. 12A illustrates a cross-section of tissue.
Figure 12B:
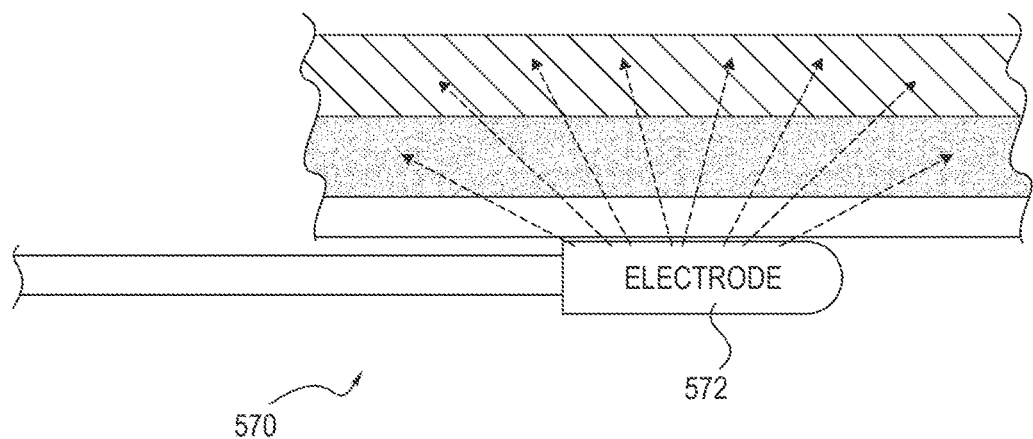
FIG. 12B illustrates heat effects of RF treatment of tissue.

Generally, when using a device 570 with an electrode 572 (e.g., monopolar RF electrode) to heat tissue, the electrode 572 must be in contact with tissue. FIG. 12A shows a cross-section of tissue. The cross-section shows a first layer or depth 702, a second layer or depth 704, and a third layer or depth 704. When the electrode 572 is activated, both the first and second layers or depths 702, 704 are heated by the current flowing from the electrode to the return (e.g., ground pad), as shown in FIG. 12B. The tissue closest to the electrode 572 receives the highest current density, and thus, the highest heat. A surface cooling mechanism may allow the temperature of the electrode surface to be reduced. Such a cooling mechanism may maintain a lower temperature at the first layer or depth 702 even though current flow will continue to heat the second layer or depth 704.

Figure 13A:
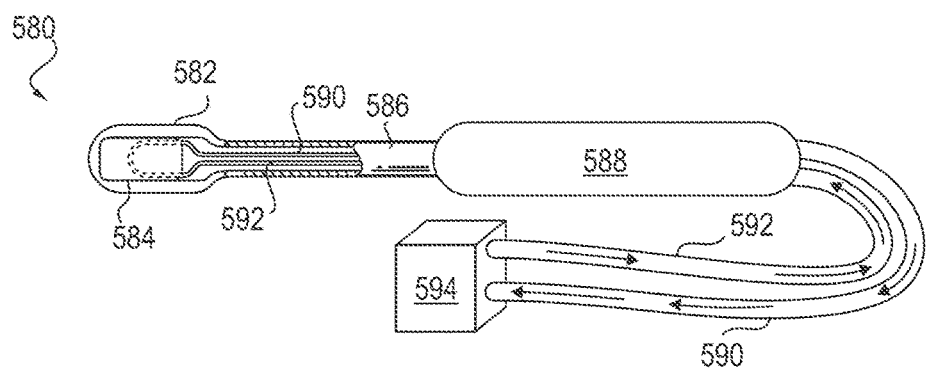
FIGS. 13A and 13B illustrate embodiments of devices for applying energy to tissue, the devices incorporating cooling systems.
Figure 13B:
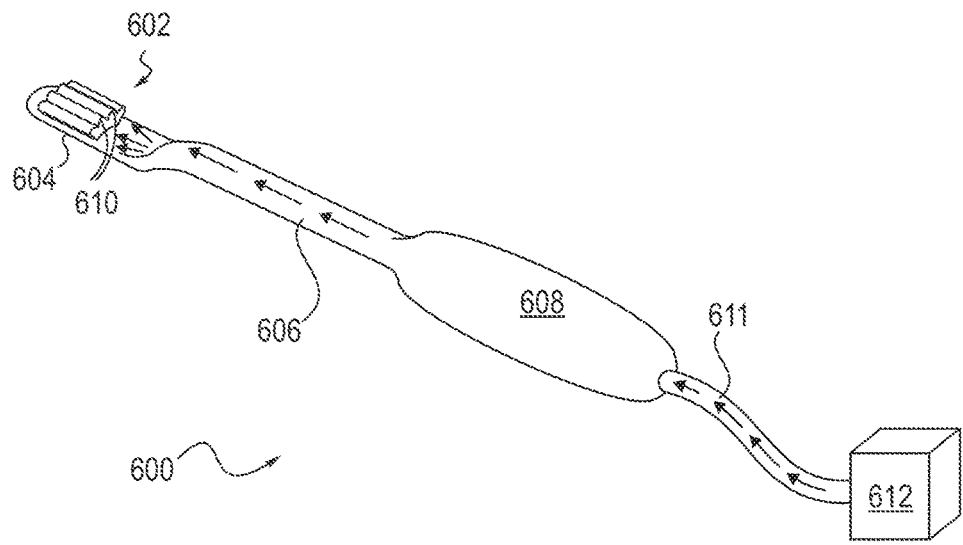

FIG. 13A depicts a device 580 configured to treat the Eustachian tube and surrounding tissue using an electrode while maintaining a reduced temperature at a first layer or depth. The device includes a treatment element 582 including an electrode 584 at the distal tip of the device 580. The treatment element 582 is attached to a distal end of a shaft 586, which is attached to the distal end of a handle 588. Input and output coolant lines 590, 592 are attached to a pump and reservoir 594 and extend into the handle 588, through the distal end of the treatment element 582 to the electrode 584 and return back through the shaft 586 and handle 588 to the pump and reservoir 594. The coolant may be remotely cooled in the reservoir and may include a fluid or gas. The coolant flowing through the electrode 584 may allow the treatment element 582 to be maintained at a reduced temperature while still allowing current flow to a deeper layers or areas of tissue. Examples of coolant include air, saline, water, refrigerants, and the like. Water may advantageously provide moderate heat capacity and be non-reactive. Refrigerants may advantageously be able to transfer significant amounts of heat through phase change. The coolant may flow through internal or external cavities of the electrode or wand tip. For example, FIG. 13B depicts an embodiment of a device 600 including a treatment element 602 with an electrode 604 at the distal tip of the device 600. The treatment element 602 is attached to the distal end of a shaft 606 which is attached to the distal end of a handle 608. The handle may be attached to a cable includes a lumen or channel 611 through which gas or fluid may flow. The lumen 611 may diverge, near the treatment element 602, into separate external channels flowing over the electrode 604. The lumen 611 and channels 610 or cavities may be attached to a fan or fluid pump 612. In some embodiments, the fan or fluid pump may remotely cool the gas or fluid.

Figure 14:
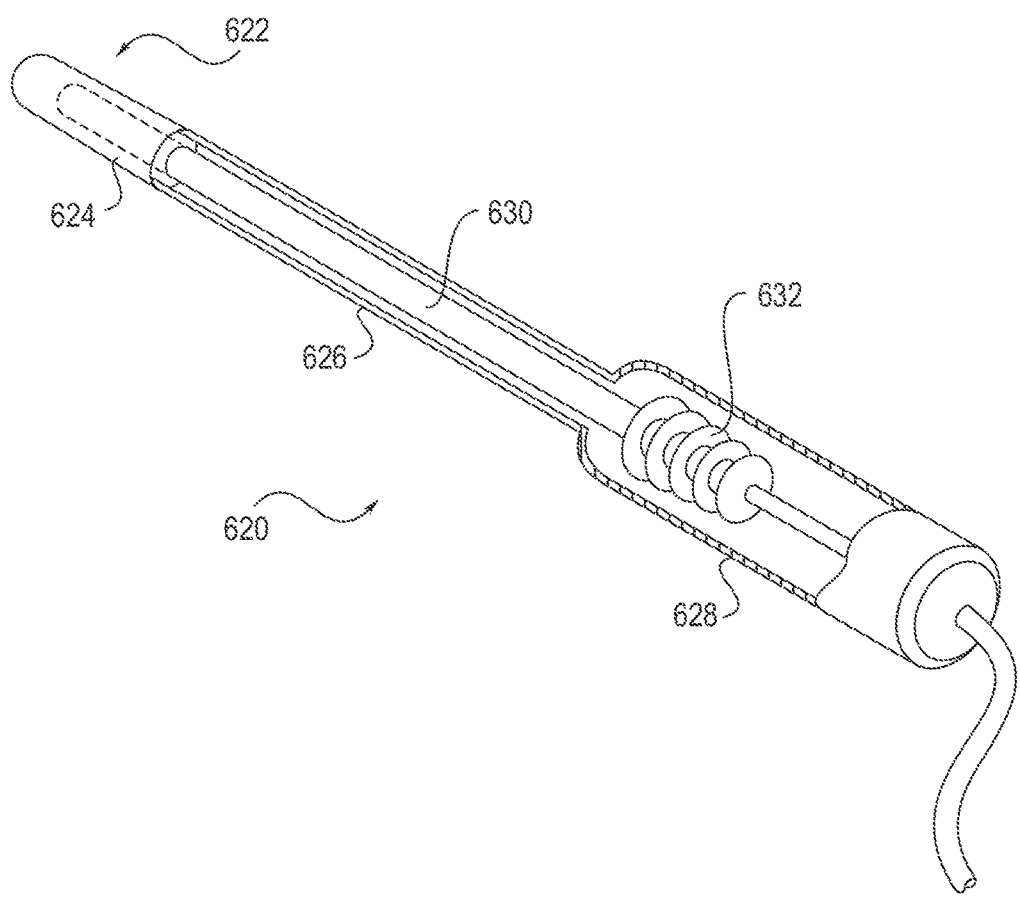
FIG. 14 shows an embodiment of a device for applying energy to tissue, the device incorporating a heat pipe.

FIG. 14 depicts another embodiment of a device 620 configured to treat the Eustachian tube or surrounding tissue using an electrode 624 while maintaining a reduced temperature at the a particular depth or layer. The device includes a treatment element 622 including an electrode 624 at its distal end. The treatment element 622 is connected to the distal end of a shaft 626 which is connected to the distal end of a handle 628. The device 620 includes a heat pipe 630 attached to the electrode 624 or treatment element 622. The heat pipe 630 is configured to transfer heat to a remote heat sink 632. As shown in FIG. 14, the heat sink 632 may be placed in the handle of the device. In some embodiments, the heat sink may be placed remotely. The heat pipe 630 may include a sealed tube (e.g., a copper tube) filled with a material that evaporates at a given temperature. When one end of the heat pipe 630 is heated, the fluid may evaporate and flow to the opposite end where it may condense and subsequently transfer heat to the heat sink 632. Using a material such as copper for the heat pipe 630 and/or heat sink 632 may advantageously provide high heat and electrical conductivity.

Embodiments may employ specific differential cooling mechanisms to maintain different and particular temperatures in adjacent tissues. The embodiments may be configured to provide more general mechanisms configured to maintain different temperatures in adjacent tissues. For example, in some embodiments, a cooling mechanism may be placed external to patient (e.g., against the patient's skin) to provide an amount of cooling.

Cooling occurring before, during, or after treatment may effect reduced temperature of tissue. In some embodiments, attaching passive fins or other structures to the electrode or wand tip may allow for heat dissipation to the surrounding air. In some embodiments, the device may be configured to spray a cool material such as liquid nitrogen before, during, or after treatment. Using a material such as copper for the passive fins or other structure may advantageously provide high heat and electrical conductivity. In some embodiments, using metals with a high heat capacity in the device (e.g., in the energy delivery element, the reshaping element, or both) may advantageously provide the ability to resist temperature change during energy delivery. In some embodiments, pre-cooling the electrode (e.g., by refrigeration, submersion, spraying with a cool substance like liquid nitrogen, etc.) may maintain a reduced temperature at a first layer or depth. Any combination of the cooling methods described herein may be used in conjunction with any of the energy delivery methods described herein (e.g., bipolar RF electrodes, arrays needles, plates, etc.).

Figure 15:
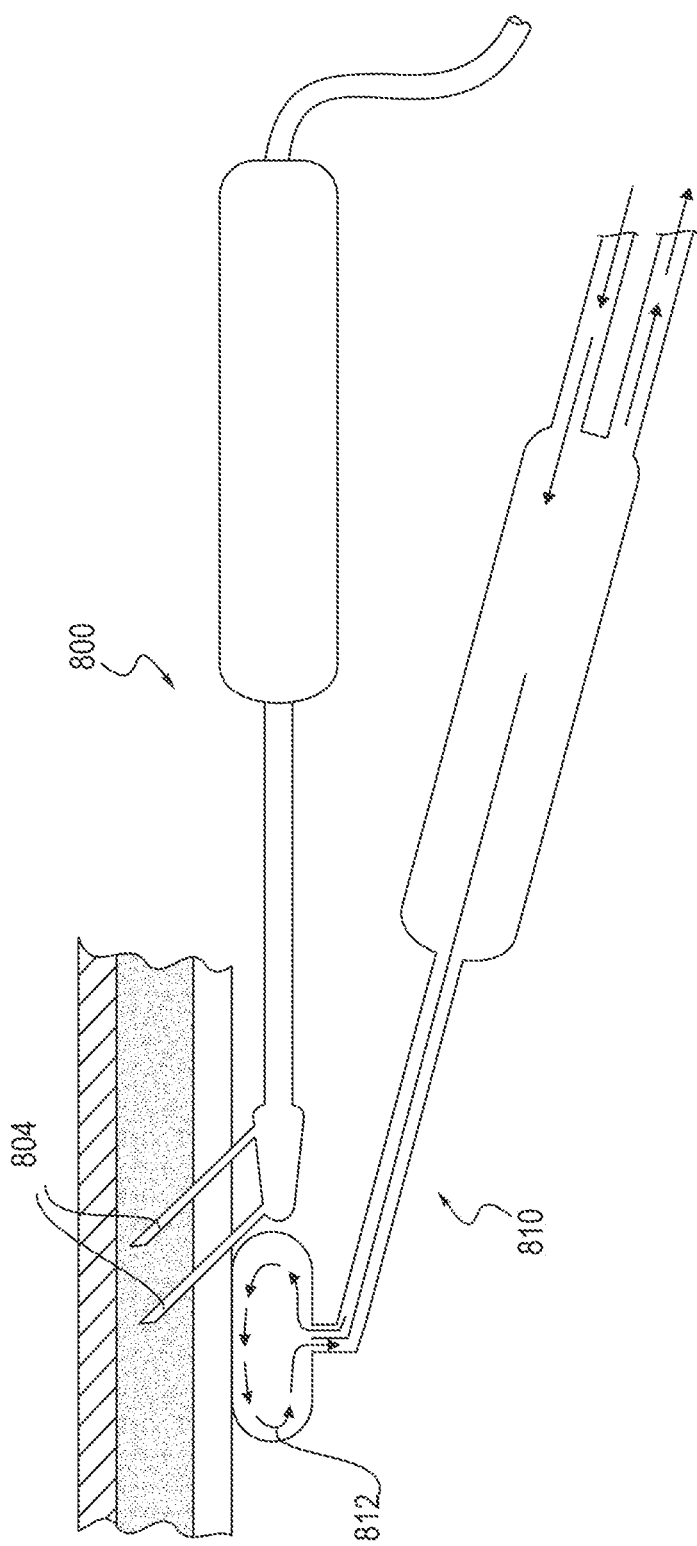
FIG. 15 shows an embodiment of a system including a device for applying energy to tissue, the device including electrode needles and a separate cooling mechanism.

FIG. 15 illustrates an example embodiment of a device 800 including a treatment element 802 including electrode needles 804 at its distal tip. The device 800 may be used in conjunction with a separate cooling device 810 which may include channels 812 or cavities to circulate air or fluid. The independent cooling device 810 may, in other embodiments, employ a different cooling mechanism.

In embodiments using laser energy to heat cartilage, it is possible to use a combination of two or more lasers whose beams converge at a location within the target tissue. This convergence may cause more heat at that junction as compared to locations where only a single beam is acting. The junction may be controlled manually or via computer control. Specific treatment may be provided.

In some embodiments, insulating material may be used to protect non-target tissue during energy delivery. For example, an electrode needle may be preferentially insulated on a portion of the needle that is in contact with non-target tissue. For another example, flat electrode blades may be insulated on a portion of the blade that is in contact with non-target tissue. Other configurations for heat isolation are also possible.

Any of the cooling mechanisms or combinations of the cooling mechanisms described herein may be used in conjunction with any of the devices or combinations of devices described herein, or the like.

Additional Examples of Methods of Treatment

Embodiments of methods for treating a Eustachian tube and surrounding tissue are now described. In one embodiment, a method of treating a Eustachian tube and surrounding tissue includes the steps of inserting an energy-delivery or cryotherapy device into a nasal passageway, and applying energy or cryotherapy to a targeted region or tissue of the nasopharynx. For example, in some embodiments, the method may include delivering energy or cryotherapy to a section of the nasopharynx in the area of the Eustachian tube. In alternative embodiments, the method may involve delivering energy to the tissue of the ear canal near the Eustachian tube.

In some embodiments, a method includes reshaping tissue. For example, such a method may include heating or delivering another energy form to a section of the Eustachian tube or surrounding tissue (e.g., cartilage) to be reshaped, applying a mechanical reshaping force to the tissue, and then removing the heat or other energy. In various alternative embodiments, the step of applying the mechanical reshaping force may occur before, during or after the step of applying heat or other energy. In one embodiment, for example, an energy delivery member having a convex treatment surface may be applied to a target tissue, and the convex treatment surface may be pushed into the tissue with sufficient force to give the tissue a concave shape. Energy may be applied to the tissue, while the force is applied, so that after the treatment device is removed, the tissue retains at least some of the concave shape. Other shape combinations are possible in alternative embodiments, and this example is provided for exemplary purposes only.

Figure 16A:
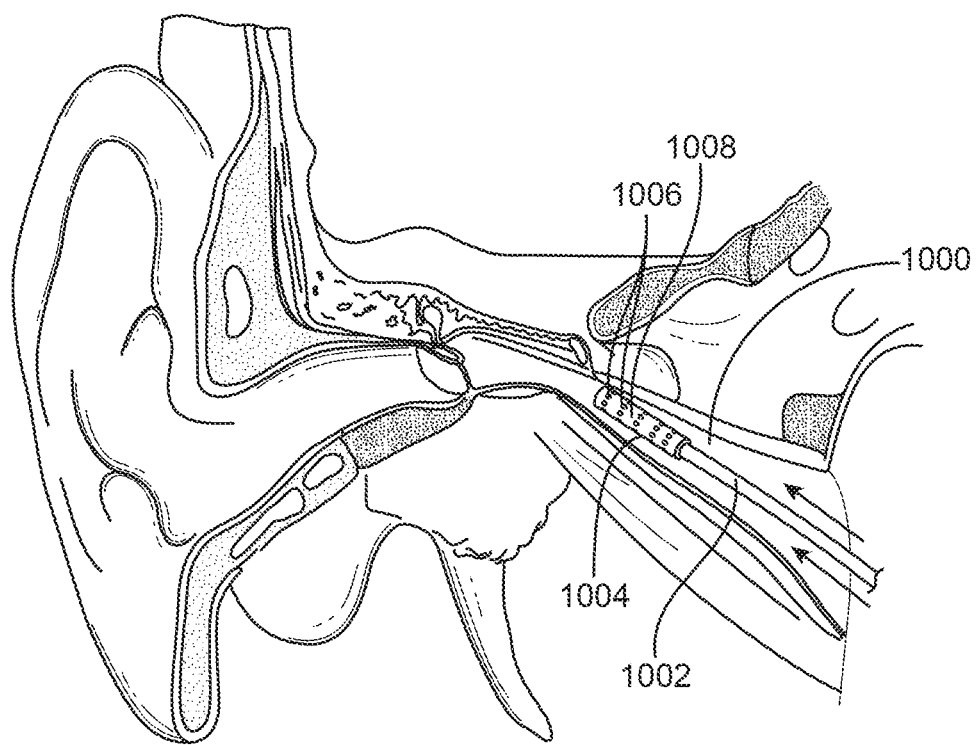
FIGS. 16A-16C illustrate an embodiment of a method for treating a Eustachian tube.
Figure 16B:
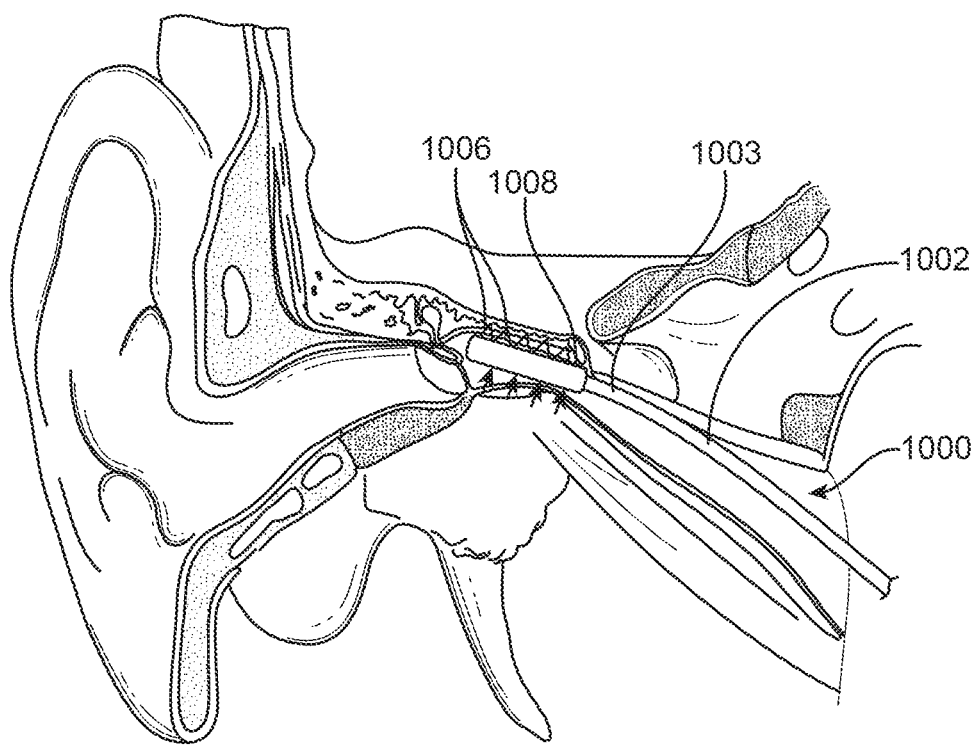
Figure 16C:
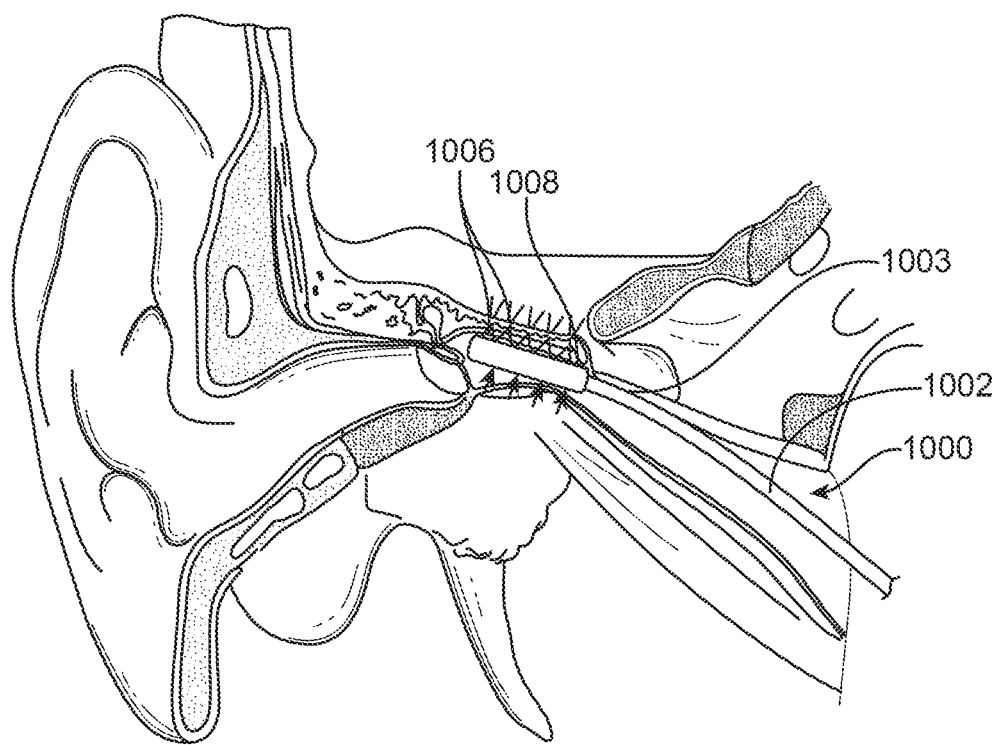

Referring to FIGS. 16A-16C, one embodiment of a method for treating a Eustachian tube is illustrated. As shown in FIG. 16A, the method may first involve advancing a Eustachian tube treatment device 1000 to a treatment area (e.g., by advancing the treatment device 1000 through a nasal passage and into the Eustachian tube). The treatment device 1000 may include a shaft 1002, a treatment portion 1004 (or "treatment element") having a tissue treatment surface 1008, and multiple energy delivery members 1006 disposed along the treatment surface 1008. In this embodiment, the energy delivery members 1006 are bipolar radiofrequency electrode needles, disposed in an array along the treatment surface 1008. In alternative embodiments, however, any of the energy delivery or removal members described in this disclosure may be used. In FIG. 16A, the treatment device 1000 is illustrated from a top/perspective view.

Referring now to FIG. 16B, the method may next involve contacting the tissue treatment surface 1008 with tissue to be treated and applying force with the treatment surface 1008 against the tissue, to temporarily deform the tissue. For example, as described herein, the tissue treatment surface 1008 may have a convex shape in some embodiments, so that when it is pressed against tissue of or near the Eustachian tube, that tissue takes on a concave shape. In FIG. 16B, the treatment device 1000 is shown in a side view, illustrating that the shaft 1002 may have a bend 1003, or alternatively multiple bends or curves. The bend 1003 may allow the treatment device 1000 to be more easily advanced into the Eustachian tube, and it may also make it easier to apply force against the tissue to be treated.

In some embodiments, the energy delivery members 1006 may be designed to pierce through mucosal tissue to apply energy to one or more deeper tissues. In the example shown, the energy delivery members 1006 are advanced into the tensor tympani muscle. Alternatively, other muscles and/or other tissues below the surface of the mucosa may be treated.

Referring to FIG. 16C, in one embodiment, the method next involves applying energy to the tissue being treated, using the energy delivery members 1006. In various embodiments, the energy may be delivered before, during and/or after application of force against the tissue with the tissue treatment surface 1004. In any such embodiment, the treated tissue may retain at least a partially reshaped configuration after the treatment device 1000 is removed from the patient.

In some embodiments, the tissue treatment device 1000 may be used once in a given Eustachian tube to treat one portion of target tissue. For example, in one embodiment, the treatment device 1000 may be used to treat an upper (cephalic) portion of tissue, in an effort to help lift the tissue of the Eustachian tube. In other embodiments, the treatment device 1000 may be used on a first portion of tissue, then moved to a second portion and used to treat that portion, then optionally moved to the third portion of tissue, and so on, as desired by the treating physician. This technique may be used, for example, to treat an entire circumference of the Eustachian tube and/or an entire length of the Eustachian tube. In yet other embodiments, a different type of tissue treatment device may be used, which covers and treats an entire circumference of the Eustachian tube at one time—for example an expandable balloon energy delivery device. Thus, in various embodiments, any suitable energy delivery device may be used on any suitable portion of Eustachian tube tissue.

Figure 17:
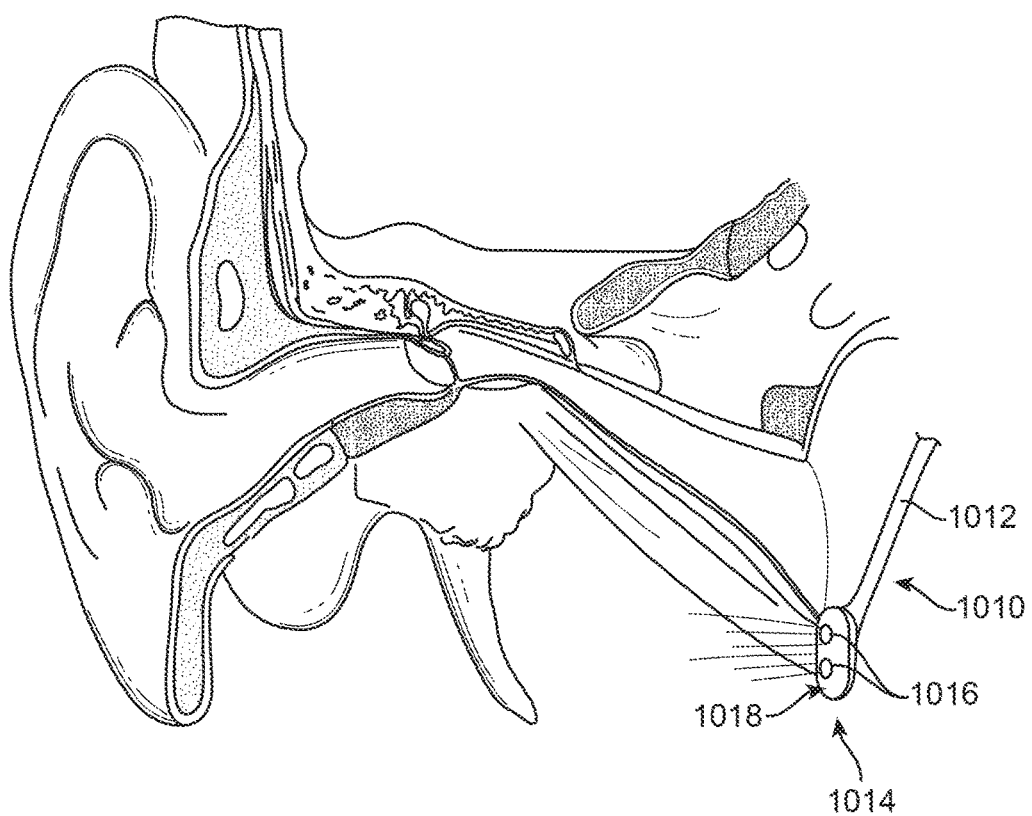
FIG. 17 illustrates an embodiment of a method for treating a Eustachian tube.

FIG. 17 illustrates an embodiment of a method for treating a Eustachian tube. The method may first involve advancing a Eustachian tube treatment device 1010 to a treatment area (e.g., by advancing the treatment device 1010 through a nasal passage and into the nasopharynx). The treatment device 1010 may include a shaft 1012, a treatment portion 1014 having a tissue treatment surface 1018, and energy delivery members 1016 disposed in an array on the treatment surface 1018. The method may next involve contacting the tissue treatment surface 1018 with tissue to be treated. The tissue to be treated may be tissue of the nasopharynx at, near, or on the Eustachian tube ostium. Contacting the tissue treatment surface 1018 with the tissue to be treated may involve applying force with the treatment surface 1018 against the tissue to temporarily deform the tissue. As illustrated in FIG. 17, the method may next involve applying energy to the tissue to be treated, using the energy delivery members 1016. As illustrated, the tissue to be treated includes tissue of the levator veli palatini muscle. In various embodiments, the energy may be delivered before, during and/or after the application of force against the tissue with the tissue treatment surface 1014. The treated tissue may retain at least a partially reshaped configuration after the treatment device is removed from the patient.

Figure 18:
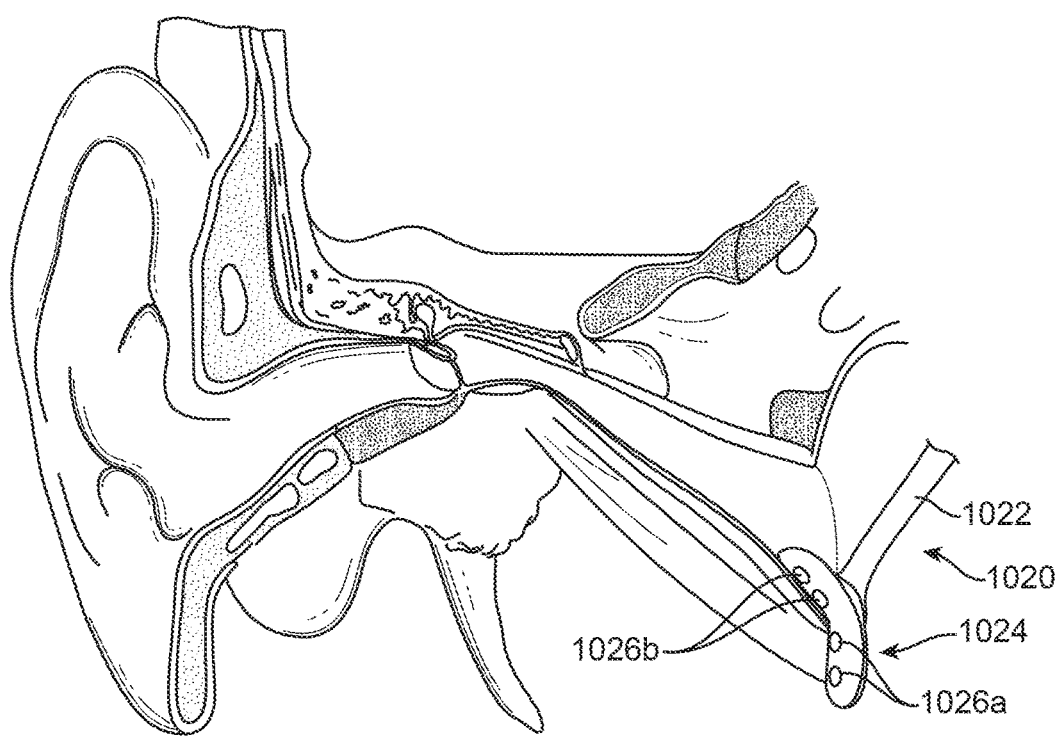
FIG. 18 illustrates an embodiment of a method for treating a Eustachian tube.

FIG. 18 illustrates an embodiment of a method for treating a Eustachian tube with a treatment device 1020. The treatment device 1020 may include a shaft 1022, a treatment portion 1024 having a tissue treatment surface 1028, and energy delivery members 1026a, 1026b disposed in an array on the treatment surface 1028. The tissue treatment portion 1024 may be curved or otherwise shaped such that a portion of the tissue treatment portion 1024 is configured to be inserted into the Eustachian tube ostium. This may facilitate positioning the device near the ostium of the Eustachian tube and facilitate treatment. For instance, one or more of the energy delivery members 1026b may be located on a portion of the treatment portion 1024 configured to be inserted into the Eustachian tube ostium, while energy delivery members 1026a may be located on a portion of the treatment portion 1024 configured to be external to the Eustachian tube. In some embodiments, energy delivery members 1026a and 1026b may correspond to first and second electrodes of a bipolar electrode pair.

The method of treating the Eustachian tube may involve advancing a Eustachian tube treatment device 1020 to a treatment area (e.g., by advancing the treatment device 1020 through a nasal passage and into the nasopharynx). The method may next involve contacting the tissue treatment surface 1028 with tissue to be treated. The tissue to be treated may be tissue of the nasopharynx at, near, or on the Eustachian tube ostium. The tissue to be treated may also include tissue within the Eustachian tube. Contacting the tissue treatment surface 1028 with the tissue to be treated may involve applying force with the treatment surface 1028 against the tissue to temporarily deform the tissue. As illustrated in FIG. 18, the method may next involve applying energy to the tissue to be treated, using the energy delivery members 1026. In various embodiments, the energy may be delivered before, during and/or after the application of force against the tissue with the tissue treatment surface 1024. The treated tissue may retain at least a partially reshaped configuration after the treatment device is removed from the patient.

Figure 19A:
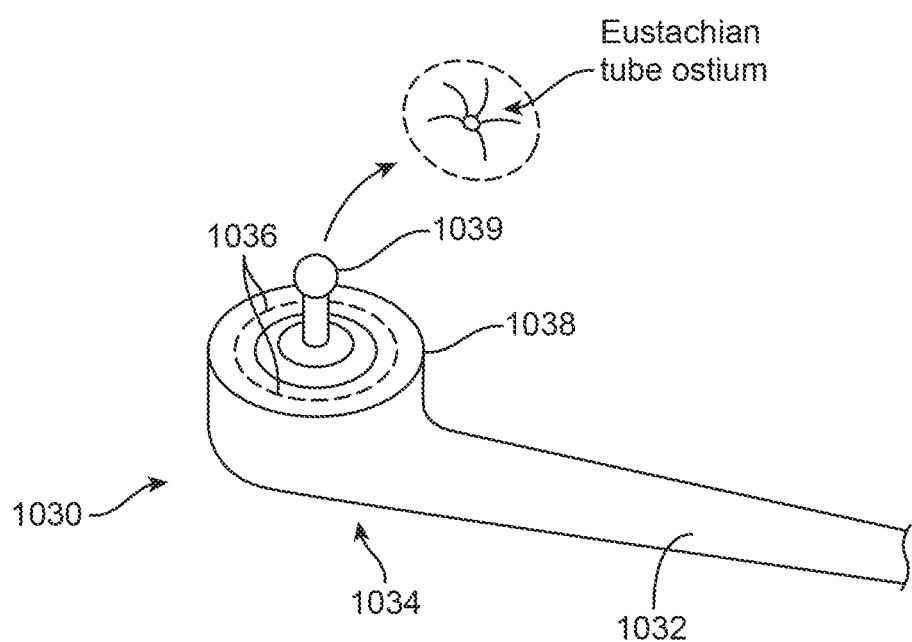
FIGS. 19A and 19B illustrate an embodiment of a device and method for treating a Eustachian tube.
Figure 19B:
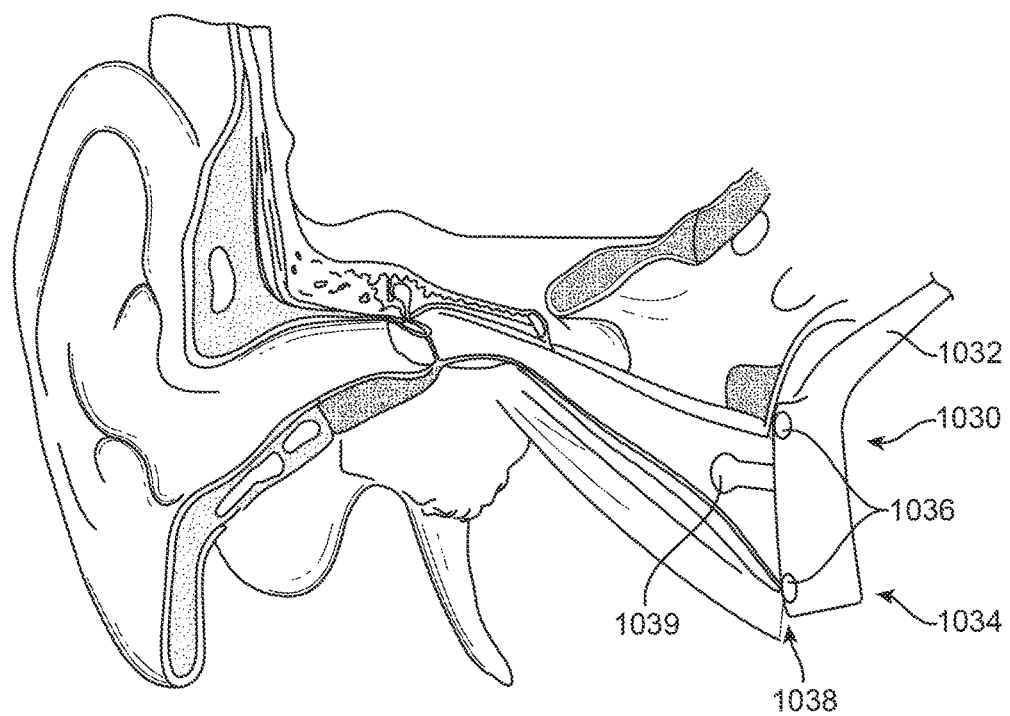

FIGS. 19A and 19B illustrate an embodiment of a method for treating a Eustachian tube with a treatment device 1030. The treatment device 1030 may include a shaft 1032, a treatment portion 1034 having a tissue treatment surface 1038, electrodes 1036 disposed in an array on the treatment surface 1038 and a passive positioner 1039 extending from the treatment portion 1034. In some embodiments, the electrodes 1036 may be bipolar electrodes. The passive positioner 1039 may be a component sized and shaped to be inserted into the Eustachian tube ostium to facilitate positioning the electrodes 1036 around the ostium. The passive positioner 1039 may be a soft and/or flexible probe that is configured to enter and align with the ostium. As illustrated, the passive positioner 1039 is an elongate protrusion with a bulb at its distal end and the electrodes 1036 are disposed on the treatment surfaced 1038 circumferentially around the passive positioner 1039. The passive positioner 1039 may facilitate positioning the device near the ostium of the Eustachian tube and facilitate treatment. In other embodiments, the passive positioner 1039 may include other shapes, such as a conical shape. In some embodiments, the passive positioner 1039 may include electrodes for treatment within the Eustachian tube. In some embodiments, the passive positioner 1039 may include a camera or other visualization device. In some embodiments, the passive positioner 1039 may include a sample-collection feature configured to collect a sample (e.g., a tissue sample). In some embodiments, the passive positioner 1039 may include a balloon that may be expanded after the passive positioner is inserted into the ostium in order to facilitate positioning, anchoring, and/or treating. The passive positioner 1039 may include other features as well.

As illustrated in FIG. 19A, the method may involve advancing the treatment device 1030 into a nasopharynx and inserting the passive positioner into the ostium of the Eustachian tube, thereby positioning the electrodes around the ostium. As illustrated in FIG. 19B, the method may next include contacting the tissue treatment surface 1038 with the tissue to be treated. The tissue to be treated may be tissue of the nasopharynx at, near, or on the Eustachian tube ostium (e.g., submucosa located just outside the ostium). Contacting the tissue treatment surface 1038 with the tissue to be treated may involve applying force with the treatment surface 1038 against the tissue to temporarily deform the tissue. The method may next involve applying energy to the tissue to be treated using the electrodes 1036.

In some embodiments, the method may further include the step of inserting a reshaping device into a nasal passageway or an ear canal after applying an energy or cryotherapy treatment. In such embodiments, a reshaping device such as an external or internal reshaping device may be applied to the patient after the treatment in order to allow for long-term reshaping of Eustachian tube and/or surrounding structures as the treated tissues heal over time.

Figure 20A:
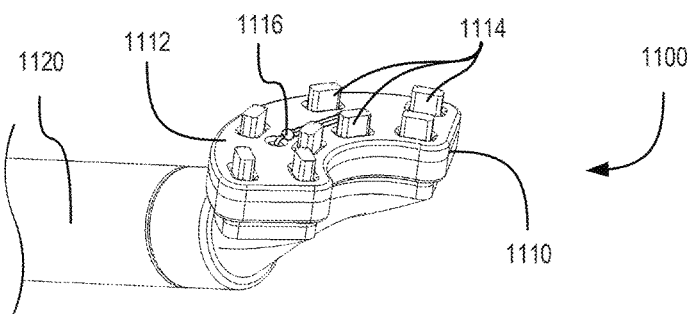
FIGS. 20A-20D illustrate an embodiment of a device having an arcuate treatment element for treating a Eustachian tube.

FIGS. 20A-20D illustrate an embodiment of a device 1100 having an arcuate treatment element 1110 for treating a Eustachian tube. Referring to FIG. 20A, the device 1100 includes the treatment element 1110 disposed at a distal end of a shaft 1120. The treatment element 1110 includes a treatment surface 1112 having multiple electrodes 1114 and a thermocouple 1116 disposed thereon.

In the illustrated configuration, the treatment surface 1112 includes a substantially flat shape, but other configurations, such as a concave shape or a convex shape, may be used. The electrodes 1114 are elongate, blunt-tipped electrodes extending from the treatment surface 1112. The electrodes 1114 can take other forms, including but not limited to needle electrodes. The electrodes 1114 can be configured as bipolar electrodes or monopolar electrodes 1114. The thermocouple 1116 can be configured to measure a surface or a sub-surface temperature of the tissue to be treated or tissue near the tissue to be treated.

Figure 20B:
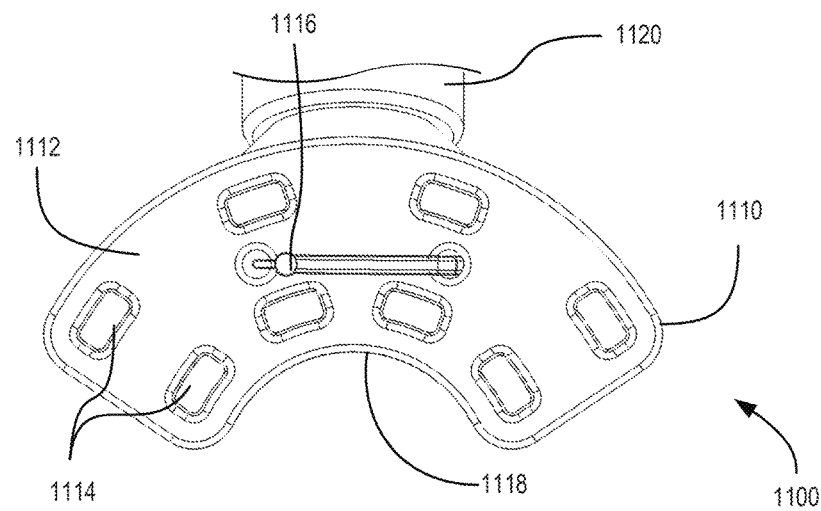

FIG. 20B illustrates a front view of the treatment element 1110. In this view, the arcuate shape of the treatment surface 1112 can be seen. In the illustrated embodiment, the treatment surface 1112 is configured to have an arc angle of approximately 112 degrees, though other configurations may be used including arc angles of between approximately 102 and 122 degrees. In some embodiments, the treatment surface 1112 may form a complete circle. The electrodes 1114 are disposed in two, parallel, arcuate rows on the treatment surface 1112.

The electrodes 1114, the treatment surface 1112, and the device 1100 as a whole can be configured (e.g., sized, shaped, or otherwise arranged) to treat tissue of or near the Eustachian tube ostium. The treatment element 1110 can define an ostium portion 1118 configured to facilitate treatment of a Eustachian tube ostium. For example, in the illustrated configuration, the treatment element 1110 and treatment surface 1112 define an ostium-portion 1118, configured as a space that can accommodate a typical size and shape of an ostium. During treatment, the treatment element 1110 can be positioned in a nasopharynx with the ostium in the ostium portion 1118 of the treatment element 1110. When so arranged, the arcuate treatment element 1110 is positioned adjacent tissue near the ostium for treatment. While the illustrated ostium portion 1118 is defined by the treatment element 1110 and lacks material, in other embodiments it need not be so configured. For example, in an embodiment, the ostium portion 1118 can include a portion of material without electrodes, insulating material, electrodes for treating the ostium directly, cooling elements to remove energy from the ostium, elements for treating within the Eustachian tube, positioning elements (e.g., a passive positioner as in FIGS. 19A and 19B), or other elements.

Figure 20C:
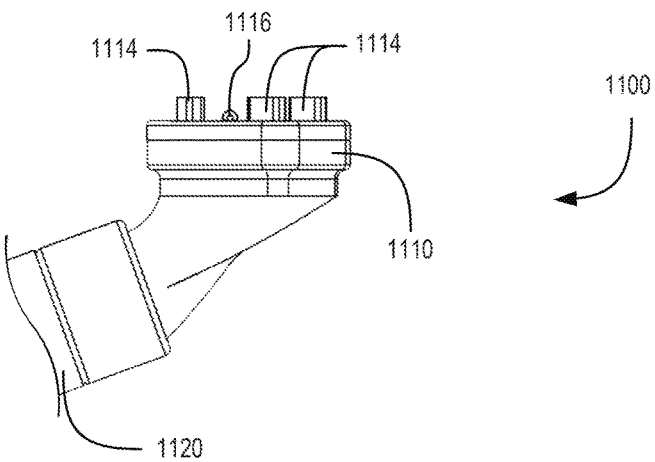

FIG. 20C illustrates a side view of the treatment element 1110. As illustrated in this view, the treatment element 1110 extends from the shaft 1120, such that treatment surface 1112 is angled relative to the shaft 1120. In the illustrated configuration, a normal of the treatment surface 1112 is angled approximately 70 degrees from a longitudinal axis of the shaft 1120 (e.g., angled approximately 70 degrees from parallel with the longitudinal axis of the shaft). In other embodiments, the angle is between approximately 60 degrees and approximately 80 degrees from the longitudinal axis of the shaft 1120. In some examples, a normal of the treatment surface 1112 is approximately perpendicular or parallel to the shaft 1120. In some examples, the configuration of the treatment element 1110 relative to the shaft 1120 is configurable by the user. In the illustrated configuration, the electrodes 1114 extend perpendicularly away from the treatment surface 1112. In some configurations, the electrodes may extend at a different angle.

Figure 20D:
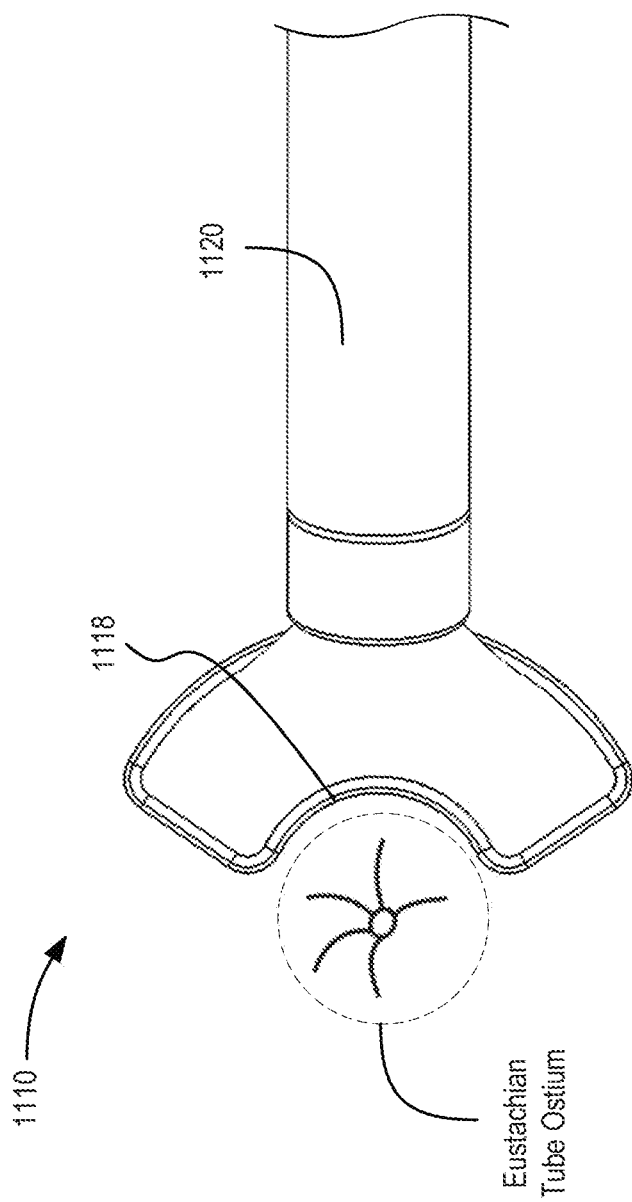

FIG. 20D illustrates a rear view of the treatment element 1110. As illustrated, the treatment element 1110 is positioned with a Eustachian tube ostium within the ostium portion 1118 of the treatment element 1110. With the device 1100 in this position, the treatment element 1110 can be used to treat tissue near the Eustachian tube ostium.

In alternative embodiments, internal and/or external reshaping devices may be used to reshape a Eustachian tube or surrounding tissue prior to the step of applying energy or cryotherapy treatments to target tissue. In some embodiments, the energy or cryotherapy treatment may be configured to change the properties of treated tissues, such that the tissues will retain the modified shape within a very short time of the treatment. In alternative embodiments, the treatment may be configured to reshape structures over time as the tissue heals.

In some embodiments, a portion of the Eustachian tube and/or associated tissue may be reshaped using a reshaping device and then fixed into place. In some embodiments, such fixation may be achieved by injecting a substance such as a glue, adhesive, bulking agent or a curable polymer into a region at or near the Eustachian tube.

In some embodiments, an injectable polymer may be injected into a region of the Eustachian tube and/or surrounding tissue, either below the skin on the exterior of the face, or under the tissue (e.g., mucosa) of the interior of the nasopharynx. In some embodiments, an injectable polymer may include a two-part mixture configured to polymerize and solidify through a purely chemical process. One example of a suitable injectable two-part polymer material is described in U.S. Patent Application Publication 2010/0144996, the entirety of which is hereby incorporated by reference. In other embodiments, an injectable polymer may require application of energy in order to cure, polymerize or solidify. A reshaping device may be used to modify the Eustachian tube and/or surrounding tissue before, after, and/or during injection of a polymer. In embodiments employing an energy-curable polymer, a reshaping device may include energy-delivery elements configured to deliver energy suitable for curing the polymer to a desired degree of rigidity.

In another embodiment, the muscles of the face are stimulated to modify the Eustachian tube prior to and/or during application of other treatments such as energy/cryo application or fixation treatments. In such embodiments, the muscles to be treated may include the muscles of the soft palate (e.g., the levator veli palatini and tensor veli palatini), muscles of the ear (e.g., tensor tympani), and/or other muscles affecting the Eustachian tube. In some embodiments, the targeted muscles may be stimulated by applying an electric current to contract the muscles, mentally by the patient, or manually by the clinician.

In some embodiments, muscles may also be selectively deactivated through chemical, ablative, stimulatory, or mechanical means. For example, muscles may be deactivated by temporarily or permanently paralyzing or otherwise preventing the normal contraction of the muscle tissue. Chemical compounds for deactivating muscle tissues may include botulinum toxin (aka "Botox"), or others. Ablative mechanisms for deactivating muscle tissue may include RF ablation, laser ablation or others. Mechanical means of deactivating muscle tissues may include one or more surgical incisions to sever targeted muscle tissue.

In some embodiments, energy may be applied to the skin of the face to effect a shrinkage of the skin, epidermis, dermis, subdermal, subcutaneous, tendon, ligament, muscle, cartilage and/or cartilage tissue. The tissue shrinkage is intended to result in a change of forces acting on the Eustachian tube to improve the Eustachian tube's function.

In another embodiment, the Eustachian tube and/or surrounding tissue may be damaged or stimulated by energy application, incisions, injections, compression, or other mechanical or chemical actions. Following such damage, a device may be used on the tissue to mold or shape the tissue during healing. In some embodiments, such a reshaping device may be temporarily placed or implanted to hold a desired shape while the patient's healing process progresses.

In some embodiments, devices may be used to provide tissue reshaping/molding and to impart energy to the Eustachian tube and/or surrounding tissue. The electrode may be placed in contact with the target tissue. The electrodes and molds may be moved to shape the tissue as necessary to achieve improvement in the Eustachian Tube. The electrodes may be activated while the tissue is deformed in the new shape to treat the tissue. The electrode may then be deactivated and the device may be removed.

If the treatment device includes a monopolar electrode or electrode needles, a ground pad may be attached to the patient. The ground pad may be attached at the patient's torso, for example the shoulder or abdomen. Other locations are also possible, such as the patient's buttocks. Preferably, the point of attachment is a large, fleshy area. After being attached, the ground pad may be plugged into a power source. If the device is powered by a remote generator (e.g., RF generator), the device may then be plugged into the generator.

Figure 1:
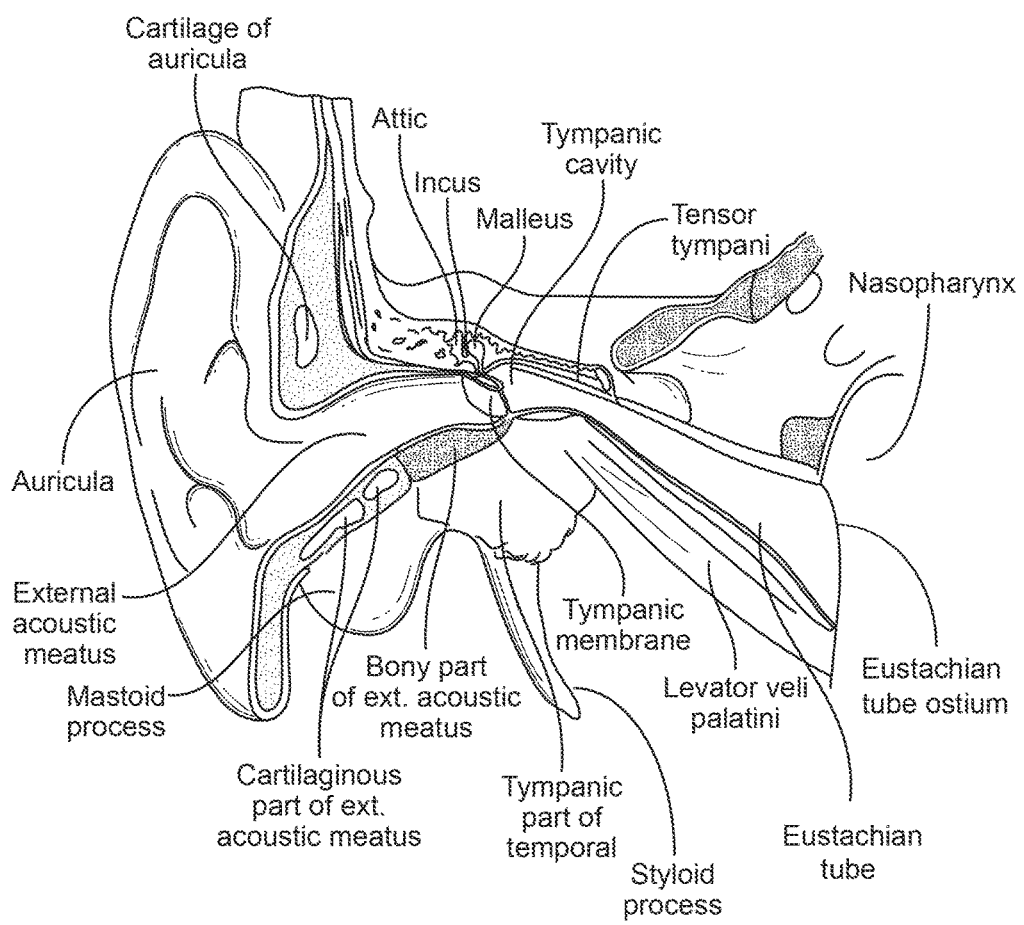
FIG. 1 illustrates an ear, including the middle ear and Eustachian tube.

A thermocouple may be provided on the electrode of a treatment element. In some embodiments, more than one thermocouple may be provided. For example, in embodiments including more than one electrode or electrode pair, each electrode or electrode pair may include a thermocouple. The thermocouple may monitor temperature of the electrode and provide feedback to a control unit (e.g., control system 42 described with respect to FIG. 1). The control unit may use the data from the thermocouple to regulate temperature and auto-shutoff once treatment has been achieved or in the case of an overly high temperature.

After treating the tissue, the device may be removed from, for example, the pharynx and/or ear canal. If a grounding pad is used, the grounding pad may be detached from the patient.

In some embodiments, differential cooling mechanisms may be used to treat the Eustachian tube and/or surrounding tissue using electrodes or other energy delivery elements while maintaining a reduced temperature at other tissue (e.g., skin and/or mucosa). The cooling system may be activated. The device may then be in contact with target tissue. The device may then be activated. Activation of the device may cause, for example, an increase in the cartilage temperature while minimizing the temperature increase in the skin and/or mucosa. The device may then be deactivated and removed.

In some embodiments, devices may be used in which insulating material is used to protect non-target tissue during energy delivery. In an embodiment, a device includes an electrode needle preferentially insulated on a portion of the needle. The needle may be inserted into the cartilage so that the insulated portion is in contact with the mucosa and/or the skin and the non-insulated portion is in contact with the cartilage. The device may be activated, causing an increase in the cartilage temperature while minimizing temperature increase in the skin and/or mucosa. The device may be deactivated and removed.

Additional Embodiments and Features

Figure 21A:
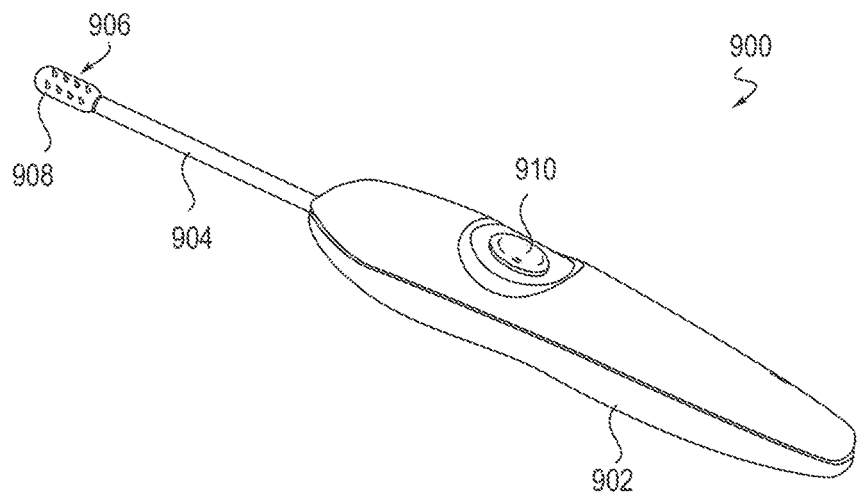
FIGS. 21A and 21B are a perspective view and a side, cross-sectional view, respectively, of an embodiment of a device for applying energy to tissue, the device including an internal power source.
Figure 21B:
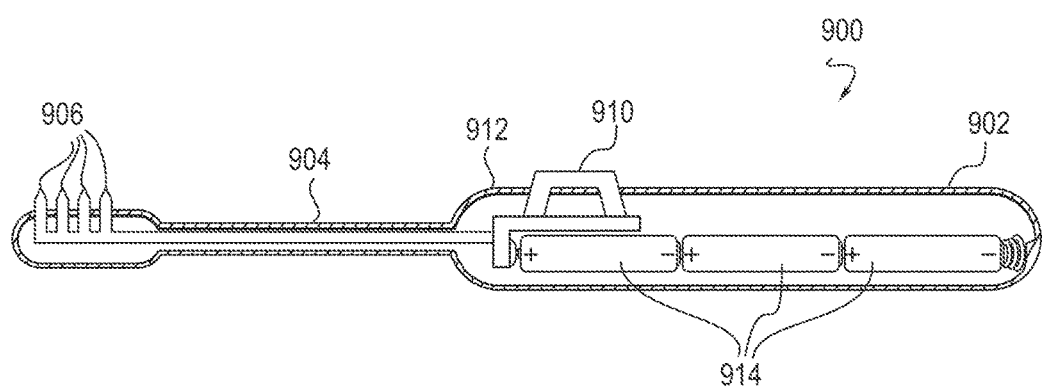

Referring now to FIGS. 21A and 21B, in one embodiment, a device 900 for treating a Eustachian tube and surrounding tissue may include an internal power source and thus be cordless. In the embodiment shown, the device 900 includes a handle 902 coupled with a shaft 904, which in turn is coupled with a treatment element 908. The handle 902 may include a power button 910 (or "on/off switch"), a circuit board (912, FIG. 9B) and a space and connections for insertion of batteries 914 as a power source. Treatment element 904 may include multiple needle electrodes 906 for applying RF energy to tissue.

Any suitable features, elements, materials or the like that have been described above may be applied to the device 900 in a similar way. In various alternative embodiments, the device 900 may include any number, size or type of batteries, depending on the size of the handle 902 and power requirements of the device 900. In some alternative embodiments, the device 900 may include an alternative power source. For example, the batteries 914 may be rechargeable in some embodiments. In other embodiments, it may be possible to plug the device 900 into a power generator for charging, and then unplug the device 900 for use. In yet other alternative embodiments, the device 900 may include a solar power collection member. The advantage of including an internal power source in the device 900 is that this eliminates the need for the device 900 to be connected, via power cord, to a large, table-top generator, as most energy delivery surgical/medical devices require. This allows a physician to perform a Eustachian tube procedure in any location or patient orientation without having to manage power cables and generators.

In some embodiments, a system for modifying a Eustachian tube may include one or more sensors. Such sensors may be used to sense any of a number of relevant tissue properties, such as temperature, impedance and the like. The sensors may be located on a treatment device in some embodiments, or alternatively they may be separate from the treatment device and positioned at or near the device during treatment. In some embodiments, the sensor(s) may provide feedback directly to the treatment device. For example if a particular tissue temperature threshold is reached, a sensor (or sensors) may send a signal to a power generator to shut down or decrease power delivered to a treatment device. In alternative embodiment, the sensor(s) may instead provide feedback to a physician or other user, so that the physician or other user can make treatment adjustments. For example, sensors may provide a warning signal when a particular tissue temperature or impedance is reached, which will help a physician know when to turn off or decrease power delivery to a treatment device. Additionally, sensor(s) may be used to sense one or more tissue properties in any suitable tissue or multiple tissues, such as but not limited to mucosa, cartilage, dermis, epidermis and other types of body soft tissue.

In an alternative embodiment, a sensor device may include a transdermal needle sensor. In another alternative embodiment, a sensor device may be attached directly to a treatment device. As illustrated by these various embodiments, sensors may be positioned either at or near a treatment location during a treatment. In some embodiments, for example, a sensor may be placed on or in epidermis while a treatment is being performed on mucosa. Alternatively, a sensor may be placed directly on mucosa during a treatment of mucosa. Additionally, in any given embodiment, multiple sensors may be placed at multiple different locations in and/or on tissue. As mentioned above, the sensor devices may, in various embodiments, provide any of a number of different types of feedback, such as feedback to a user, feedback to a power generator, or both.

Referring now to FIG. 22, in some embodiments, a treatment device 950 may include a treatment element 952 with wings 954 extending laterally from it. The wings 954 are configured to help direct the treatment element 952 into a particular treatment location/position and/or to prevent the treatment element 952 from contacting tissue that the physician does not want to treat. The wings 954 may be configured to help prevent the treatment element 952 from being advanced too far. Alternative embodiments may include additional wings or other protrusions or shapes to prevent contact particular structures. Some embodiments may include adjustable wings or wings that expand once the electrodes have been placed. Any other size, shape or configuration of one of more wings may be included, according to various embodiments.

Referring to FIGS. 23A-23C, in various alternative embodiments, treatment elements of treatment devices may have different shapes and/or sizes for addressing different types and/or shapes of tissue. For example, as shown in FIG. 23A, in one embodiment, a treatment element 960 of a device may have a square or rectangular profile with a flat distal end, which may be ideal for addressing relatively flat tissue configurations. Two electrodes 962 (or two sets of electrodes) may be used to send an arc of current (e.g., RF current) through tissue in the pattern shown by the multi-headed arrow.

In another embodiment, as shown in FIG. 23B, a treatment element 970 may have an oval profile with a curved distal end. Two electrodes 972 or sets of electrodes send a current through tissue in an arc. This configuration may be advantageous for addressing tissue having a curved profile. In yet another embodiment, as shown in FIG. 23C, a treatment element 980 may have a flatter curved profile, for example for addressing tissue with a curved shape but not as sharp of an angle as the tissue shown in FIG. 23B. Again, the electrodes 982 send energy through the curved tissue in a curved arc.

As is evident from FIGS. 23A-23C, a treatment element of a treatment device may have any suitable configuration for advantageously addressing any tissue type and shape. In some embodiments, multiple different treatment devices, each having a differently shaped treatment element, may be provided, and a user may select a treatment device for a particular tissue type and/or shape, based at least in part on the shape of the treatment element of the device.

In various alternative embodiments, a treatment device for Eustachian tube and surrounding tissue may use a treatment modality that does not involve delivery of energy to, or removal of energy from, tissue. For example, in some embodiments, the treatment device may create some kind of mechanical injury to one or more tissues to cause a change in shape and/or one or more properties of the tissue. The expandable balloon embodiment described above is one example. Other examples may include, but are not limited to, needles, micro-needles, blades or the like, any of which may be used to cause scar tissue formation and/or tissue contraction. Other embodiments may use sclerotherapy, involving injecting one or more substances (acid, coagulants, etc.) into the target tissue to induce scar tissue formation and/or other changes in the tissue properties. In some cases, one type of tissue (for example, mucosa) may be transformed into a different type of tissue altogether (for example, scar tissue). In other examples, a one or more properties of the tissue may be changed without changing the overall type of tissue. For example, the tissue may be caused to shrink, contract, stiffen and/or the like. One advantage of these non-energy-based embodiments is that they do not require a source of energy. This may make them easier to use and possibly to manufacture and supply.

In other embodiments, thermal energy may be applied to the Eustachian tube or surrounding tissue by applying the energy from an external location, rather than an internal location within, for example, an airway of a patient. For example, in some embodiments, a treatment device may be positioned on the skin of a patient and used to deliver thermal energy through the epidermis to the deep subdermal and/or dermal layer near the Eustachian tube or surrounding tissue. In some embodiments, the treatment device may also be used to cool the superficial dermis and epidermis, for example. This delivery of energy could, in some embodiments, act to tighten tissue. In an alternative embodiment, instead of using thermal energy to change the tissues, a treatment device may use mechanical means, such as micro-needles, to create a subdermal tissue response, such as scarring, for a similar type of tissue tightening effect.

In yet other embodiments, some methods for treating a Eustachian tube or surrounding tissue may include applying a gel, paste, liquid or similar substance to a surface of a tissue during an energy delivery treatment of tissue. Such substances may be applied to target tissue, such as mucosa, non-target tissue, such as epidermis, or a combination of both. The substance (or substances) applied may serve any of a number of different purposes, such as but not limited to modifying conductivity of tissue and providing anesthetic effect. Conductivity enhancing substances may improve the efficiency and/or consistency of energy delivery (such as but not limited to RF energy). Alternatively or additionally, one or more substances may be injected into tissue. For example, saline, Lidocaine, other anesthetic agents, or any other suitable agents, may be injected. Some embodiments may involve applying one substance and injecting another substance.

In other alternative embodiments, it may be possible to achieve desired changes in tissue properties and/or shapes by injecting substance or applying substance only—in other words, without also applying energy. For example, injecting a sclerotherapy substance into tissue may, in some embodiments, achieve a desired tissue result. In additional alternative embodiments, a method of treating a Eustachian tube or surrounding tissue may include injecting a substance into nasal tissue and then curing the substance in order to change the substance's properties and, in turn, at least one of the nasal tissue's properties. A treatment device may be used to cure the substance. In some embodiments, the treatment device may be used to deform the target tissue and cure the substance, while the tissue is deformed, so that the tissue retains approximately the same, deformed shape after the substance is cured and the treatment device is removed. In another alternative embodiment, a surface-based biodegradable agent may be applied and cured to change the shape of the target nasal tissue.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A device for modifying a Eustachian tube, the device comprising:
   a shaft comprising a proximal end and a distal end and defining a longitudinal axis;
   a handle attached to the proximal end of the shaft;
   a treatment element extending at an angle from the distal end of the shaft, relative to the longitudinal axis, the treatment element comprising;
      a flat tissue treatment surface having an arcuate shape with an arc angle and comprising;
         an inner edge having a first radius of curvature; and
         an outer edge having a second radius of curvature that is larger than the first radius of curvature; and
      a first arcuate row of electrodes disposed on the flat tissue treatment surface closer to the inner edge than the outer edge, such that the first arcuate row of electrodes faces an ostium of the Eustachian tube when positioned for treatment;
      a second arcuate row of electrodes disposed on the flat tissue treatment surface closer to the outer edge than the inner edge, wherein the second arcuate row of electrodes is parallel with the first arcuate row of electrodes; and
      a thermocouple disposed between the first arcuate row of electrodes and the second arcuate row of electrodes.

2. The device of claim 1, wherein the shaft is an elongate, flexible shaft, sized and shaped to be inserted through a patient's nostril to reach the ostium of the Eustachian tube.

3. The device of claim 1, wherein the electrodes of the first arcuate row and the electrodes of the second arcuate row comprise elongate, blunt-tipped, bipolar, radiofrequency electrodes extending out of the flat tissue treatment surface.

4. The device of claim 1, wherein the angle of the flat treatment element relative to the shaft positions the flat tissue treatment surface is between 60 degrees and 80 degrees from parallel with the longitudinal axis of the shaft.

5. The device of claim 1, wherein the arc angle of the arcuate shape of the treatment element is between 102 degrees and 122 degrees.

6. The device of claim 1, wherein the electrodes of the first arcuate row and the electrodes of the second arcuate row comprise elongate, bipolar, radiofrequency needle electrodes extending out of the flat tissue treatment surface.

* * * * *